US006204052B1

(12) United States Patent
Bout et al.

(10) Patent No.: US 6,204,052 B1
(45) Date of Patent: Mar. 20, 2001

(54) ADENOVIRAL VECTORS WITH REDUCED TNF RESPONSE AND PARTIAL E3 REGION DELETION

(75) Inventors: Abraham Bout, Moenkepelle; Dirk W. Van Bekkum, Rotterdam; Domenico Valerio, Leiden, all of (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 08/515,495

(22) Filed: Aug. 15, 1995

(30) Foreign Application Priority Data

Aug. 16, 1994 (EP) .................................................. 94202322

(51) Int. Cl.[7] ............................. C12N 5/00; C12N 15/00; A61K 48/00; A01N 63/00
(52) U.S. Cl. ........................ 435/320.1; 435/325; 424/93.2
(58) Field of Search ........................... 435/320.1, 172.3, 435/240.1, 240.2; 514/44, 2; 424/93.1, 93.21, 93.2

(56) References Cited

U.S. PATENT DOCUMENTS

| 5,631,236 | 5/1997 | Wood et al. ............................ 514/44 |
| 5,670,488 | 9/1997 | Gregory et al. . |

FOREIGN PATENT DOCUMENTS

| WO90/07936 | 7/1990 | (WO) . |
| WO93/19191 | 9/1993 | (WO) . |
| WO94/12649 | * 12/1993 | (WO) . |
| WO 94/12649 | 6/1994 | (WO) . |
| WO94/28152 | 12/1994 | (WO) . |
| WO95/05835 | 3/1995 | (WO) . |
| WO95/09654 | 4/1995 | (WO) . |
| WO95/10623 | 4/1995 | (WO) . |
| WO95/14101 | 5/1995 | (WO) . |
| WO95/14102 | 5/1995 | (WO) . |
| WO 95/34671 | 12/1995 | (WO) . |
| WO 97/00326 | 1/1997 | (WO) . |

OTHER PUBLICATIONS

"Restricted Changes in the Adenovirus DNA–Binding Protein That lead to Extended Host Range or Temperature–Sensitive Phenotypes" by D.E. Brough, S.A. Rice, S. Sell and D.F. Kelessig—Journal of Virology, Jul. 1985, pp. 206–212.
"Multiplication of Viruses—An Overview" by B. Roizman—Virology, Second Edition 1990—pp. 28, 29, 87 & 88.
"Ablation of E2A in Recombinant Adenoviruses Improves Transgene Persistance and Decreases Inflammatory Response in Mouse Liver" by J.F. Engelhard, X. Ye, B. Doranz and J.M. Wilson—Proc. Nat. Acad. Sci. USA vol. 91, pp. 6196–6200 (Date No Available).
Bett, A., et al., *Virus Research* (1995) 39:75–82.
Ballay, A., et al., *EMBO J.* (1985) 4:3861–3865.
Gilardi, P., et al., *FEBS Lett.* (1990) 267:60–62.
Gingras, MC., et al., *Cancer Gene Ther.* (1996) 3:151–154.
Shenk, T., et al., *Curr. Top. Microbiol. Immunol.* (1984) 111:1–39.
Stratford–Perricaudet, L., et al., *J. Clin. Invest.* (1992) 90:626–630.
Stratford–Perricaudet, L., et al., *Human Gene ther.* (1990) 1:241–256.
Wills, K., et al., *Human Gene Ther.* (1994) 5:1079–1088.
Bout, A., et al., *Human Gene Therapy* (1994) 5:3–10.
Cohen, D. R., et al., *Nucl. Acids Res.* (1986) 14:3641–3658.
Culver, K.W., et al., *Science* (1992) 256:1550–2.
Engelhardt, J.F., et al., *Human Gene Therapy* (1993) 4:759–769.
Ginsberg, H.S., et al., *Proc. Natl. Acad. Sci. USA* (1989) 86:3823–3827.
Ginsberg, H.S., et al., *Proc. Natl. Acad. Sci. USA* (1991) 88:1651–1655.
Haddada, H., et al., *Human Gene Therapy* (1993) 4(6):703–11.
March, S.R., et al., *Nature* (1985) 315:641–646.
Levrero, M., et al., *Gene* (1991) 101(2):195–202.
McKnight, S.L., *Nucl. Acids Res.* (1980) 8:5949–5964.
Precious, B. and Russell, W.C., *Virology: a practical approach* (Mahy, B., ed) (1985) pp. 193–205, Revaen Press Ltd., Washington, D.C.
Prince, G.A., et al., *J. Virol* (1993) 67(1):101–111.
Simon, R.H., et al., *Human Gene Therapy* (1993) 4:771–780.
Spergel, J.M. and Chen–Kiang, S. *Proc. Natl. Acad. Sci. USA.*, (1991) 6472–6476.
Spergel, J.M., et al., *J. Virol.* (1992) 66(2):1021–1030.
Stratford–Perricaudet, L.D. and Perricaudet, M. *Human Gene Transfer* (1991) (Cohen–Adenauer, O., and Boiron, M., eds) vol. 219, pp. 51–61, Hohn Libbey Eurotext.
Wold, W.S.M. and Gooding, L.R. *Virology* (1991) 184:1–8.
Yang, Y., et al., *Nat. Genet* (1994) 7(3):362–9.
Yang, Y., et al., *Proc Natl Acad Sci USA* (1994) 91(10):4407–11.
Zöller, M., et al., *Int. J. Cancer* (1992) 50:450–457.
Lui et al (1994) Cancer Res. 54, 3662–3667.*

(List continued on next page.)

*Primary Examiner*—Deborah Crouch
(74) *Attorney, Agent, or Firm*—Trask Britt

(57) ABSTRACT

Adenoviral vectors with a deletion of the E3 region such that the remaining E3 region reduces the TNF response of a host mammalian cell infected with the virus. The portion of the E3 region remaining in these vectors encodes the 14.7 kD protein, and may also contain a deletion of at least the E1a promoter. These partially deleted E3 vectors will inhibit the host cell's immune response so that the infected cell will live longer. Any non-adenoviral gene expressed from these vectors in the infected cell will be produced for a longer length of time and achieve a higher concentration than when adenoviral vectors not expressing function 14.7 kD protein are used. These 14.7 kD expressing adenoviral vectors will be useful for gene therapy and especially in cancer gene therapy where the non-adenoviral DNA sequence being expressed are preferably cytokine genes, such as IL-1, and suicide genes, such as HSV-tk. The vectors also are useful for antisense therapy.

34 Claims, 18 Drawing Sheets

OTHER PUBLICATIONS

Anderson (1994) Human Gene Therapy 5, 281–282.*
Science (1995) vol. 269, pp. 1050–1055.*
Blau et al (Nov. 2, 1995) New Eng. J. Med., 12–41207.*
Mulligan (1993) Science 260, 926–932.
Blaese et al (1994) Europ. J. Cancer 30A, 1190–1193.
Vieweg et al (1995) Cancer Invest. 13, 193–201.
Mullen (1994) Pharmac. Therap. 63, 199–207.
Zabnet et al (1993) Cell 75, 207–216.*
Chen et al (1994) Proc. Natl. Acad. Sci. 91, 3054–3057.*
Graham et al., Methods Mol. Biol., Jul., 1991, 109–128.*
Rosenfeld et al., Cell, 68, 1992, 143–155.*
Fujiwara et al., Cancer Res., 54, 1994, 2287–2291.*
Liu et al., Cancer Res., 54, 1994, 3662–3667.*
Stratford–Perricaudet et al., Bone Marrow Transp., 9(1), 1992, 151–152.*
Neve, Trends Neurosci., 16(7), 1993, 251–253.*
Stratford–Perricaudet, Human Gene Transfer, 219, 1991, 51–61.*
Zhang et al., Cancer Gene Therapy, 1(1), 1994, 5–13.*
Le Gal La Salle et al., Science, 259, 1993, 988–990.*
Rosenfeld et al., Science, 252, 1991, 431–434.*
Haddada et al., Human Gene Ther., 4, 1993, 703–711.*
Wills et al., J. Cell. Biochem., 1993, Supp. 17E–17F, 204, 5216.*
Wills et al., J. Cell Biochem., 1994, 18C, 204, N524.*
Haj–Ahmad et al., J. Virology, 57(1), 1986, 267–274.*
Marshall, Science, 269, 1995, 1050–1055.*
Miller et al., FASEB J., 9, 1995, 190–199.*
Culver et al., TIG, 10(5), 1994, 174–178.*
Hodgson, Exp. Opin. Ther. Pat., 5(5), 1995, 459–468.*
Stratford–Perricaudet et al., Human Gene Transfer 219:51–61 1991.*
Levrero et al., Gene 101(2):195–202, 1991.*

* cited by examiner

ATGGCTTCGTACCCCTGCCATCAGCACGCGTCTGCGTTCGACCAGGCTGCGCGTTCTCG
CGGCCATAGCAACCGACGTACGGCGTTGCGCCCTCGCCGGCAGCAAGAAGCCACGGAAG
TCCGCCTGGAGCAGAAAATGCCCACGCTACTGCGGGTTTATATAGACGGTCCCCACGGG
ATGGGGAAAACCACCACCACGCAACTGCTGGTGGCCCTGGGTTCGCGCGACGATATCGT
CTACGTACCCGAGCCGATGACTTACTGGCAGGTGCTGGGGGCTTCCGAGACAATCGCGA
ACATCTACACCACACAACACCGCCTCGACCAGGGTGAGATATCGGCCGGGGACGCGGCG
GTGGTAATGACAAGCGCCCAGATAACAATGGGCATGCCTTATGCCGTGACCGACGCCGT
TCTGGCTCCTCATATCGGGGGGAGGCTGGGAGCTCACATGCCCCGCCCCCGGCCCTCA
CCCTCATCTTCGACCGCCATCCCATCGCCGCCCTCCTGTGCTACCCGGCCGCGCGATAC
CTTATGGGCAGCATGACCCCCCAGGCCGTGCTGGCGTTCGTGGCCCTCATCCCGCCGAC
CTTGCCCGGCACAAACATCGTGTTGGGGGCCCTTCCGGAGGACAGACACATCGACCGCC
TGGCCAAACGCCAGCGCCCCGGCGAGCGGCTTGACCTGGCTATGCTGGCCGCGATTCGC
CGCGTTTACGGGCTGCTTGCCAATACGGTGCGGTATCTGCAGGGCGGCGGGTCGTGGCG
GGAGGATTGGGGACAGCTTTCGGGGACGGCCGTGCCGCCCCAGGGTGCCGAGCCCCAGA
GCAACGCGGGCCCAGCACCCCATATCGGGGACACGTTATTTACCCTGTTTCGGGCCCCC
GAGTTGCTGGCCCCCAACGGCGACCTGTACAACGTGTTTGCCTGGGCCTTGGACGTCTT
GGCCAAACGCCTCCGTCCCATGCACGTCTTTATCCTGGATTACGACCAATCGCCCGCCG
GCTGCCGGGACGCCCTGCTGCAACTTACCTCCGGGATGATCCAGACCCACGTCACCACC
CCAGGCTCCATACCGACGATCTGCGACCTGGCGCGCACGTTTGCCCGGGAGATGGGGGA
GGCTAACTGA

Fig. 1  Nucleotide sequence of HSV-TK.

Construction of pMLP.TK

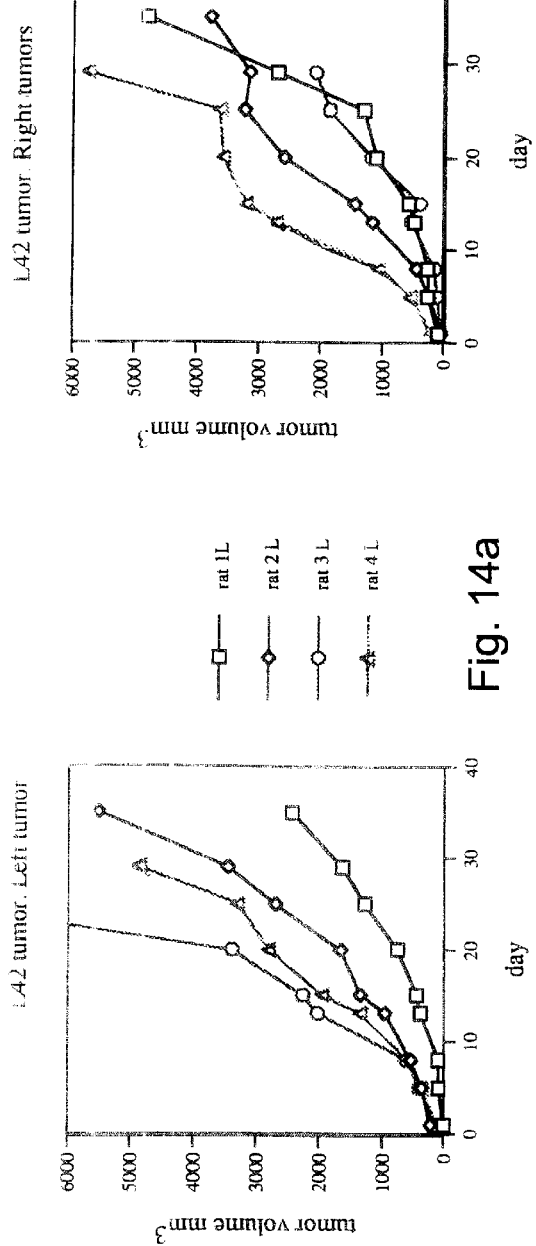
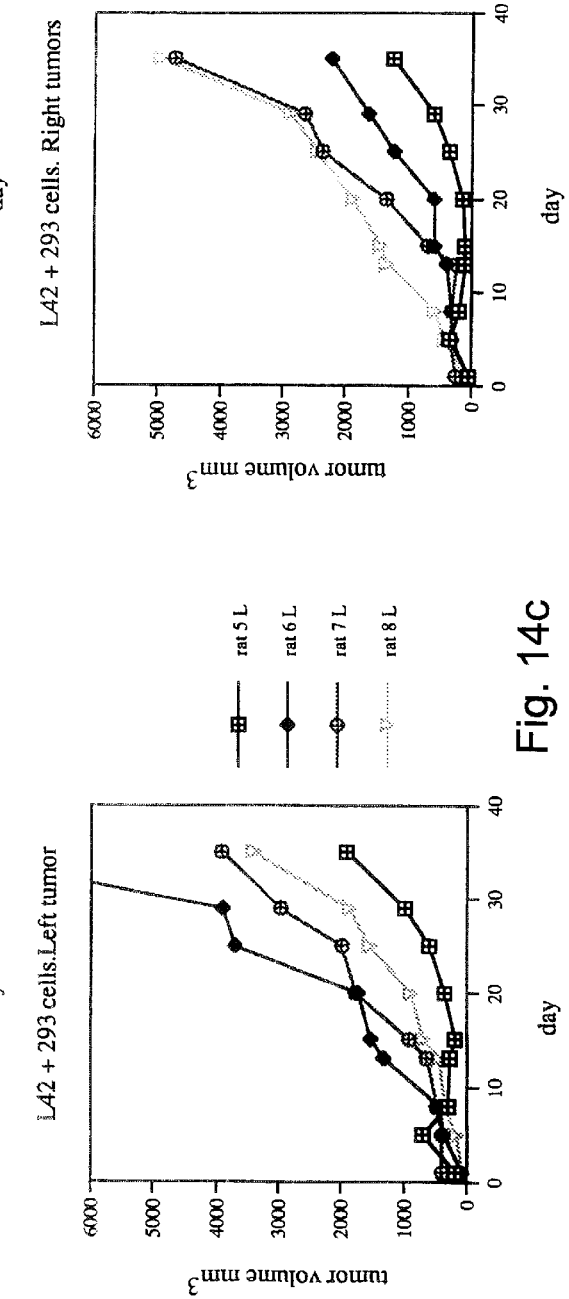
Fig. 14a
Fig. 14b
Fig. 14c
Fig. 14d

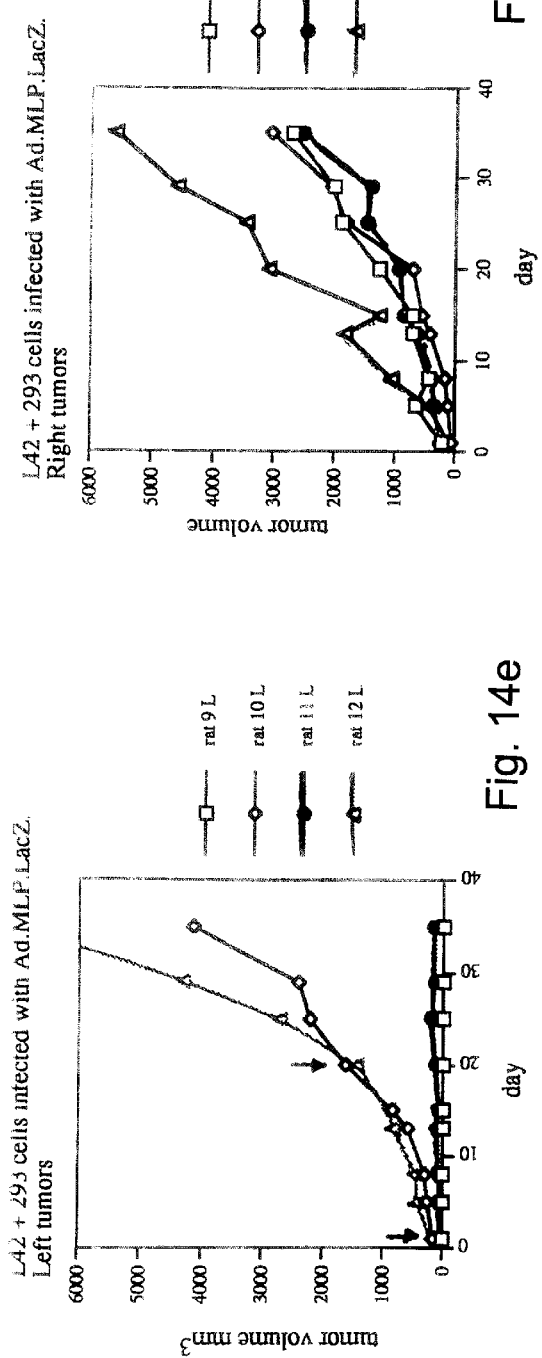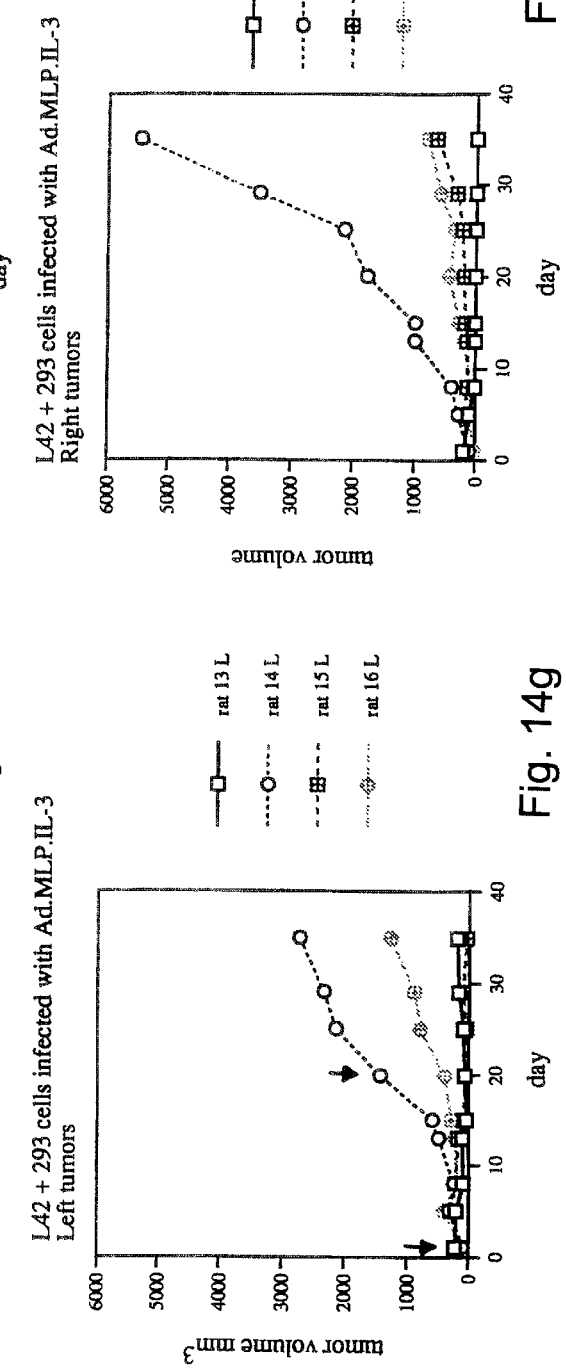

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (xi) SEQUENCE DESCRIPTION: SEQ ID NO: 1:

CTCTAAGCTT GAAGCGCGCG TATGGCTTCG      30

(2) INFORMATION FOR SEQ ID NO: 2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (xi) SEQUENCE DESCRIPTION: SEQ ID NO: 2:

ACACTCTAGA GTGTTTCAGT TAGCCTCC      28

(2) INFORMATION FOR SEQ ID NO: 3:

(i) SEQUENCE CHARACTERISTICS:
      (A) LENGTH: 1131 base pairs
      (B) TYPE: nucleic acid
      (C) STRANDEDNESS: unknown
      (D) TOPOLOGY: unknown (ii) MOLECULE TYPE: DNA (genomic)

(iii) HYPOTHETICAL: NO (xi) SEQUENCE DESCRIPTION: SEQ ID NO: 3:

ATGGCTTCGT ACCCCTGCCA TCAGCACGCG TCTGCGTTCG ACCAGGCTGC GCGTTCTCGC      60

```
GGCCATAGCA ACCGACGTAC GGCGTTGCGC CCTCGCCGGC AGCAAGAAGC CACGGAAGTC      120

CGCCTGGAGC AGAAAATGCC CACGCTACTG CGGGTTTATA TAGACGGTCC CCACGGGATG      180

GGGAAAACCA CCACCACGCA ACTGCTGGTG GCCCTGGGTT CGCGCGACGA TATCGTCTAC      240

GTACCCGAGC CGATGACTTA CTGGCAGGTG CTGGGGCTT  CCGAGACAAT CGCGAACATC      300

TACACCACAC AACACCGCCT CGACCAGGGT GAGATATCGG CCGGGACGC  GGCGGTGGTA      360

ATGACAAGCG CCCAGATAAC AATGGGCATG CCTTATGCCG TGACCGACGC CGTTCTGGCT      420

CCTCATATCG GGGGGAGGC  TGGGAGCTCA CATGCCCCGC CCCCGGCCCT CACCCTCATC      480

TTCGACCGCC ATCCCATCGC CGCCCTCCTG TGCTACCCGG CCGCGCGATA CCTTATGGGC      540

AGCATGACCC CCCAGGCCGT GCTGGCGTTC GTGGCCCTCA TCCCGCCGAC CTTGCCCGGC      600

ACAAACATCG TGTTGGGGGC CCTTCCGGAG GACAGACACA TCGACCGCCT GGCCAAACGC      660

CAGCGCCCCG GCGAGCGGCT TGACCTGGCT ATGCTGGCCG CGATTCGCCG CGTTTACGGG      720

CTGCTTGCCA ATACGGTGCG GTATCTGCAG GGCGGCGGGT CGTGGCGGGA GGATTGGGGA      780

CAGCTTTCGG GGACGGCCGT GCCGCCCCAG GGTGCCGAGC CCCAGAGCAA CGCGGGCCCA      840

GCACCCCATA TCGGGGACAC GTTATTTACC CTGTTTCGGG CCCCCGAGTT GCTGGCCCCC      900

AACGGCGACC TGTACAACGT GTTTGCCTGG GCCTTGGACG TCTTGGCCAA ACGCCTCCGT      960

CCCATGCACG TCTTTATCCT GGATTACGAC CAATCGCCCG CCGGCTGCCG GGACGCCCTG     1020

CTGCAACTTA CCTCCGGGAT GATCCAGACC CACGTCACCA CCCCAGGCTC CATACCGACG     1080

ATCTGCGACC TGGCGCGCAC GTTTGCCCGG GAGATGGGGG AGGCTAACTG A              1131

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 4:

AGCTTGAATT CCCGGGTACC T                                                21

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (xi) SEQUENCE DESCRIPTION: SEQ ID NO: 5:

CTAGAGGTAC CCGGGAATTC A                                                21

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

(ii) MOLECULE TYPE: other nucleic acid (iii) HYPOTHETICAL: NO (xi) SEQUENCE DESCRIPTION: SEQ ID NO: 6:

CAGCAAAGAA GTCAAGATGG CC                                              22

(2) INFORMATION FOR SEQ ID NO: 7:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (xi) SEQUENCE DESCRIPTION: SEQ ID NO: 7:

GTGAGACTCC AGACCTACGC CTGG                                            24

(2) INFORMATION FOR SEQ ID NO: 8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (xi) SEQUENCE DESCRIPTION: SEQ ID NO: 8:

ACAAAGCTTT GGAGGACCAG                                                 20

(2) INFORMATION FOR SEQ ID NO: 9:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid (iii) HYPOTHETICAL: NO (xi) SEQUENCE DESCRIPTION: SEQ ID NO: 9:

ATGAGGATCC TTCAGGCTCC A                                               21

(2) INFORMATION FOR SEQ ID NO: 10:

(i) SEQUENCE CHARACTERISTICS:
             (A) LENGTH: 571 base pairs
             (B) TYPE: nucleic acid
             (C) STRANDEDNESS: unknown
             (D) TOPOLOGY: unknown (ii) MOLECULE TYPE: cDNA (iii) HYPOTHETICAL: NO (xi) SEQUENCE DESCRIPTION: SEQ ID NO: 10:

AAGCTTTGGA GGACCAGAAC GAGACAATGG TTCTTGCCAG CTCTACCACC AGCATCCTCT     60
GTATGCTGCT CCCGCTCCTG ATGCTCTTCC ACCAGGGACT CCAGATTTCA GACAGGGGCT    120

-continued

| | | | | | |
|---|---|---|---|---|---|
|CAGATGCCCA|CCATTTACTC|AGGACGTTGG|ATTGCAGGAC|TATTGCCTTG|GAGATTTTGG 180|
|TGAAGCTCCC|ATATCCTCAG|GTATCTGGAC|TCAATAATAG|TGACGACAAA|GCCAATCTGA 240|
|GGAATAGTAC|CTTGCGGAGA|GTAAACCTGG|ACGAATTCCT|AAAAAGCCAA|GAGGAGTTTG 300|
|ATTCTCAGGA|CACAACGGAC|ATCAAGTCCA|AACTTCAGAA|ACTTAAGTGT|TGTATTCCTG 360|
|CAGCTGCGAG|CGACTCTGTG|TTGCCAGGTG|TCTACAATAA|AGATCTGGAT|GACTTTAAGA 420|
|AGAAACTGAG|ATTCTACGTG|ATCCATCTTA|AGGACCTGCA|GCCAGTGTCA|GTCTCTAGAC 480|
|CACCTCAGCC|CACATCTAGC|TCTGACAACT|TTCGCCCTAT|GACCGTGGAA|TGTTAAAACA 540|
|GCAGGCAGAG|CAACTGGAGC|CTGAAGGATC|C| |571|

ADENOVIRAL VECTORS WITH REDUCED TNF RESPONSE AND PARTIAL E3 REGION DELETION

The invention relates to the field of recombinant DNA technology, more in particular to the field of gene therapy.

In particular the invention relates to novel vectors, especially for use in gene therapy, although they can be used for other recombinant expression purposes such as in providing transgenic animals.

Gene therapy is a recently developed concept for which a wide range of applications can be and have been envisaged.

In gene therapy a molecule carrying genetic information is introduced in some or all cells of a host, whereby the genetic information is added to the genetic information of the host in a functional format.

The genetic information added may be a gene or a derivative of a gene, such as a cDNA, which encodes a protein. In this case the functional format means that the protein can be expressed by the machinery of the host cell.

The genetic information can also be a sequence of nucleotides complementary to a sequence of nucleotides (be it DNA or RNA) present in the host cell.

The functional format in this case is that the added DNA (nucleic acid) molecule or copies made thereof in situ are capable of base pairing with the complementary sequence present in the host cell. Alternatively the added DNA or copies thereof in situ could interact with proteins present in the cells Applications include the treatment of genetic disorders by supplementing a protein or other substance which is, through said genetic disorder, not present or at least present in insufficient amounts in the host, the treatment of tumors and (other) acquired diseases such as (auto)immune diseases or infections, etc.

As may be clear from the above, there are basically two different approaches in gene therapy, one directed towards compensating a deficiency present in a (mammalian) host and the other directed towards the removal or elimination of unwanted substances (organisms or cells).

The invention provides vectors which are suitable for both kinds of gene therapy.

A problem associated with the introduction of any foreign material into mammalian hosts, especially via systemic routes, is that there is always a risk of inducing an immune response. This is also true in gene therapy. If the genetic information is provided through a medium which may lead to an immune-response, the result will be that such genetic information will never be incorporated into the target cells, or that it will be incorporated, but that the cells will be eliminated by the immune system.

In both cases neither kind of gene therapy will be efficacious, since the new genetic information will only be available for a very short period of time. Moreover, repeated treatments will be impossible.

For the purpose of gene therapy, adenoviruses carrying deletions have been proposed as suitable vehicles.

Adenoviruses are non-enveloped DNA viruses. The genome consists of a linear, double stranded DNA molecule of about 36 kb[32]. Recombinant adenovirus vectors have been generated for gene transfer purposes. All currently used adenovirus vectors have a deletion in the E1 region, where novel genetic information can be introduced. The E1 deletion renders the recombinant Virus replication defective. It was demonstrated that recombinant adenoviruses are able to efficiently transfer recombinant genes to airway epithelium of rhesus monkeys (1,2). In addition, we have observed a very efficient adenovirus mediated gene transfer to a variety of tumor cells in vitro and to solid tumors in animals models (lung tumors, glioma) and human xenografts (lung tumors) in immunodeficient mice in vivo.

In contrast to for instance retroviruses, adenoviruses a) do not integrate into the host cell genome; b) are able to infect non-dividing cells and c) are able to transfer recombinant genes in vivo extremely efficiently. Those features make adenoviruses attractive candidates for in vivo gene transfer of for instance suicide and/or cytokine genes into tumor cells. Recently, in vitro adenovirus mediated gene transfer of Il-2 was reported (3).

As disclosed in for instance WO93/19191, the E3 region of the virus, which is not essential for growth of the virus in vitro, nor for infection in vivo, has also been deleted from the viral vector.

For a better understanding of the present invention a brief description of the E3 region is given below (reviewed in (4)).

Nine mRNAs from the E3 region are identified in group C adenoviruses (group C=Ad2 and Ad5 commonly cause cold-like respiratory infections)(5). From some of the mRNAs, the corresponding proteins have been identified. Proteins encoded by this area have molecular weights of 19, 14.7, 11.6, 10.4 and 6.7 kDa). Group B adenoviruses apparently encode two E3 proteins (20.1 and 20.4 kD) that are not found in group C adenoviruses. None of the E3 proteins is required for adenovirus replication in cultured cells or in acute infections of the lungs of hamsters or cotton rats. Despite this, E3 is always maintained in natural isolates of adenoviruses (4). A short description of the function of some E3 proteins is presented (4–6):

A function of the 19 kDa protein, called gp 19K because it is a glycoprotein, is to protect adenovirus infected cells against MHC class-I restricted cytotoxic T-cell lysis. This glycoprotein complexes intracellularly with Class I histocompatibility antigens, thereby reducing recognition of the infected cell by the cellular immune system.

Another protein of the E3 region (14.7 kDa) is responsible for suppression of cytolysis induced by TNF. TNF is secreted by activated macrophages and lymphocytes and is cytotoxic or cytostatic to certain tumor cells (see for review (6)). TNF also lyses cells infected with certain viruses and is released during infections by influenza virus. It has been shown that mouse C3HA fibroblasts are lysed by TNF when infected by adenovirus mutants that lack region E3. Uninfected cells are not lysed by TNF, nor are cells infected by wild-type adenovirus. Mutant recombinant adeoviruses that do not express E3-10.4K, E3-14.5K and E3-14.7K induced increased infiltration of neutrophils. Vaccinia virus vectors have been generated that express E3-14.7K, TNF or both proteins. The vectors expressing TNF were less virulent in mice than control vectors, whereas E3-14.7K increased the virulence of the TNF expressing vectors. This led to the conclusion that E3-14.7K counteracts the antiviral effect of TNF in vivo.

The 10.4 kDa and 14.5 kDa proteins encoded by the E3 region function in concert to down-regulate the EGF receptor (tyrosine-kinase) in adenovirus-infected cells. Stimulation of the kinase activity of EGF-R results in the activation of cellular metabolism and eventually in the induction of DNA synthesis and mitosis.

The biological significance of EGF-R downregulation is unknown. It has been suggested that 10.4K/14.5K mimic EGF in activating the kinase activity of EGF-R which could be a mechanism by which adenovirus activates quiescent cells. Alternatively, perhaps the purpose of 10.4/14.5 K is to eliminate EGF-R, so that it cannot signal. Elimination of these receptors should preclude an inflammatory response induced by EGF (6).

Other functions than those known so far might be provided by E3. It is of interest that it has been demonstrated that deletion of the E3 region leads to a more rapid replication and increased toxicity as compared to recombinant adenoviruses in which the E3 has been replaced by other genes, that do not have E3 like properties. It should be noted that both strands of adenovirus contain protein coding sequences. The sequences at the opposite of E3 on the 1 strand space the E4 and E2 regions. Although no known transcripts are derived from this area, it does not exclude that deletion has consequences for virus replication.

Mutants that have an intact E1 region, but whose E3 region is largely deleted, were found to replicate like wild-type virus in the cotton rats lungs, but the lymphocyte and macrophage/monocyte inflammatory response was markedly increased. Onset of viral multiplication, which reached maximum titers 2–4 days after infection was soon followed by progressively increasing peribronchial, perivascular and alveolar septal infiltration of lymphocytes and monocyte/macrophages and finally by lymphocytic infiltration of the basal bronchiolar wall into the epithelium (5,7).

Based on experiments with mice, which are nonpermissive for human adenovirus replication, it was concluded that only early genes need to be expressed to produce pneumonia (8). These data led to the findings that the early inflammatory pathological events predominantly result from production of cytokines, mainly TNF-alpha, whereas the late (i.e., 5–7 days) peribronchial and perivascular lymphocytic infiltration is the result of a cytotoxic T-cell response. When the E3 region is deleted the pathological response is markedly increased (5,7,8).

Viruses lacking expression of E3 14.7 kD protein display the early pathological response (5).

The invention provides improved adeno viral vectors for gene therapy, which do not have a number of drawbacks associated with viral vectors disclosed for this purpose sofar.

The invention provides recombinant vectors derived from an adenovirus wherein at least the E1 region of the DNA encoding the adenovirus has been deleted and wherein at least a functional part of the E3 region is present in said vector.

As stated above, the E3 region is dispensable for growth of adenovirus in vitro and for infection with adenovirus in vivo. Recombinant adenoviruses are expected not to express any adenoviral gene because of the deletion of the immediate early E1 region, because this region is essential for adenoviral expression and DNA replication (9). It was noticed, however, that there is a subtype of cells that are able to express adenoviral genes and even can support low levels replication of E1 deleted adenovirus (10). Certain cellular factors, expressed in a number of cell types, are able to substitute for the E1 region of adenovirus, and mediate expression of adenoviral genes and adenoviral DNA replication (10,11). For example, it was found that E2a protein of adenovirus was synthesized in cells of the lungs of a baboon after being infected with recombinant adenovirus that was lacking E1 and E3 (12), which was accompanied with an inflammatory response in the lungs (13).

The observed inflammatory response was similar as that found after administration of replication competent virus to rodents (5,7,8,14,15).

In the mouse liver, expression of E2a protein after infection with E1/E3 deleted adenoviruses was associated with a CTL response against infected cells and thus rapid loss of recombinant gene expression (16). Similar effects were observed after delivery of E1/E3 deleted adenovirus vectors in cotton rat lungs (15).

Also a number of tumor cells can support limited synthesis of adenoviral proteins in the absence of E1 (10). One of the aims therefore is to design recombinant adenoviruses that do not give rise to a host response agains adenovirus infected cells. Therefore, recombinant adenoviruses should be developed that are able to circumvent the host cell response that is elicited against E3 deleted vectors.

For this purpose, we constructed adenoviruses in which the E3 region is retained (see examples hIl-1a, rIl-3 and Ad.TK). Although the E3 region is dispensable in recombinant viruses, our reason for making viruses retaining this region is that those cells that are able to support low levels of adenovirus gene expression and/or replication, and hence are sensitive to a host cell response, will also express low levels of the E3 proteins. Because the E3 proteins are capable or preventing or reducing host cell responses against infected cells, recombinant vectors containing E3 are superior to vectors that are E3 deleted.

This will be an advantage for both gene therapy of inherited disorders as for acquired diseases such as cancer. For example, in pre-clinical testing of gene therapy of Cystic Fibrosis in rhesus monkeys, E1 and E3 deleted recombinant adenoviruses caused peribronchial lymphocytic infiltrates and interstitial pneumonia in the alveolar area of the lungs (1). For gene therapy of Cystic Fibrosis such adverse pathological changes are very undesirable, because of loss of gene expression and adverse effects to patients. The inflammatory reactions are most likely caused by expression of adenovirus proteins in infected cells in this area of the lungs, as similar findings were observed after administration of E1/E3 deleted recombinant viruses in baboon lungs (12). In the latter case, synthesis of adenovirus proteins (e.g. E2a and hexon) was observed Such adverse effects might be prevented by using recombinant adenovirus vectors that are E1 deleted, but that retain the E3 region.

In vivo administration of recombinant adenoviruses for treatment of cancer might result in gene transfer to a significant number of normal cells. For example, in clinical studies for malignant glioma we envisage to administer recombinant adenovirus in the wound-bed after debulk of the tumor mass by surgery. It will be clear that transduction of normal brain cells is unavoidable. Destruction of normal cells by an immune reaction is to be avoided, in particular when non-regenerating tissues such as the brain are involved. Furthermore, it might be that non-dividing normal cells expressing e.g. HSV-tk add to the so-called bystander effect by synthesis of phosphorylated ganciclovir which consequently is taken up by tumor cells, leading to tumor cell kill. Lysis of such cells then would decrease the anti-tumor effect of suicide gene therapy.

In addition to responses against normal cells, also host responses against adenovirus infected tumor cells are to be expected, because tumor cells in particular are able to support synthesis of adenovirus proteins and low levels of adenovirus replication (10). Therefore, to have a maximal effect of the therapeutic gene (e.g. cytokine or suicide gene) a host response, in particular the early response which is prevented by the 14.7 kD protein, against adenovirus encoded proteins is unwanted. For cytokine gene transfer, an immune response against tumor antigens should be elicited. Therefore, immune reponses against adenovirus encoded proteins should be avoided. The same holds for the suicide gene therapy, e.g. by the introduction of an HSV-TK gene into a tumor. The salient aspect of this kind of gene therapy is that only 10% of tumor cells have to express the TK gene to destroy a tumor (17) (the bystander effect). (Early) Destruction of the TK expressing cells would prevent the bystander effect. Therefore, also for cancer suicide gene therapy adenovirus vectors containing E3 will be superior to E3 deleted vectors. Accordingly, we have constructed recombinant adenoviruses that are deleted for E1 but do contain the E3 region (see Ad.hIl-1a, Ad.rIl-3 and Ad.TK examples).

To summarize, E3 containing vectors will be superior to their E3 deleted counterparts because they are able to prevent or reduce host cells responses such as CTL lysis of adenovirus infected cells and cell lysis by TNF.

It will be understood that it may not be necessary to retain the whole E3 region in the vectors according to the invention, as long as the part retained still has the function of reducing the response of the host against infected cells. For example, expression of E3-14.7 kD alone might be sufficient to reduce early responses mediated by TNF see e.g. (5) or (8).

As stated before these vectors are very useful for gene therapy of inherited diseases such as cystic fibrosis, Duchenne molecular dystrophy, Hypercholesterolemia, blood clotting disorders (hemophilia) and the like.

As also stated before they are very useful in the therapy of acquired diseases, such as tumors, hepatitis, (auto) immune diseases, restinosis and the like.

Depending on the disease to be treated various genes or derivatives of genes can be incorporated in the vectors according to the invention. These genes need not be genomic, cDNA can also be used. It will also be possible to construct genes which encode not the natural protein of interest but a loner acting or more stable variant thereof, so called muteins. It may also be sufficient to incorporate only a part of a gene or a derivative thereof.

A wide variety of encoding genes may be applied. They include but are not limited to factors in the blood clotting cascade (such as factor VIII or factor IX), cytokines such as Il-1, Il -2, Il -3, etc., TNF, antibodies directed against tumor markers, optionally as fusion proteins with endotoxins, suicide genes such as HSV thymidine kinase, or cytosine deaminase, tPA, etc.

As stated before it need not be necessary to include a gene encoding a protein for gene therapy purposes. Often transcription of a sequence complementary to a sequence of the host may be employed in so called antisense therapy strategies.

The vectors according to the invention may contain regulatory elements such as promoters and enhancers derived from adenovirus itself, but these elements may also be derived from other species such as cytomegalovirus, Rous sarcoma virus (LTR) or for instance the polyadenylation signal of SV40.

The invention in a preferred embodiment provides tumor therapy using the suicide gene thymidine kinase of Herpes Simplex Virus (HSV-TK).

In another preferred embodiment the invention provides gene therapy of tumors using the cytokines IL-1 or Il-3.

The invention will be illustrated in greater detail using these two approaches as examples. Cancer gene therapy by the introduction of cytokine genes into tumor cells In the past years, a completely new approach to enhance the immune response against solid experimental tumors has been described. The concept underlying this approach is to have cytokines produced at high levels inside the tumor, while systemic concentrations remain low, thereby reducing or preventing the toxic side effects of cytokines. The effect of transfer of cytokine genes into tumor cells has been studied in a variety of rodent tumor models. The local inflammatory response generated by the cytokine producing tumor cells resulted in regression of the tumor in various studies, e.g. after retrovirus mediated transduction of murine tumor cells with the gene for Il-1, IFN-g, IFN-a, Il-2, Il-4, Il-7, TNF, G-CSF and GM-CSF (18). Tumor rejection after transduction with the cytokine genes mentioned above was T-cell dependent, and in some studies cytotoxic immune responses were also generated against non-transduced cells of the same tumors (parent cells), that had been implanted in the same mouse. E.g., transfer of the gene for IFN-g into murine fibrosarcoma cells resulted in IFN-g producing tumor cells. Following transplantation of these transduced cells, long lasting, T-cell mediated immunity occurred as judged by rejection of subsequently inoculated, untransduced tumor cells (19).

Immuno Gene-therapy Using Il-1

More than 20 years ago it seemed that immunotherapy would add significantly to the prognosed survival time of lung cancer patients, when a striking improvement of survival was reported in patients in whom empyema developed after surgical resection for carcinoma of the lung (20,21). The reaction between immune lymphocytes and bacterial antigens was believed to activate macrophages to destroy residual tumor cells through an immunologically non-specific mechanism. These analyses were obviously retrospective. As it was not ethically justified to induce empyema on purpose in resected patients, several studies were performed using intrapleural deposition of BCG. The initially promising results (22,23) could not be substantiated in subsequent randomized trials (24–27). A variety of other immunostimulatory treatments, as an adjuvant to surgery, have been studied. Among those, long-term treatment with levisamole and in particular treatment with specific tumor associated antigens in combination with Freund adjuvant have been reported to result in significant improvements by a few authors, but not by others (28,29). Such observations seem to hold promise that activation of immune reactions and perhaps even more so of the ensuing lymphokine mediated inflammatory processes in and around the tumor, may attract macrophages and lymphocytes capable of killing substantial numbers of tumor cells, a process that has been termed carcinolysis. These expectations are substantiated by many other studies in laboratory animals carrying transplantable tumors.

Il-1 is one of the central mediators of immune inflammatory responses (30). Therefore, inflammatory responses as described above were assumed to be evoked by production of Il-1 by tumor cells. Some tumor cell lines can be induced to produce Il-1 by treatment of the cells with lipopolysaccharides (LPS). Results of such studies were described by Zoller et al (31), who observed rejection of tumor cells when they were induced to produce Il-1 by treating them with LPS prior to injection in the animals. In addition, when the tumor cells were transfected with a DNA expression construct encoding the pro-Il-1a protein, they also observed rejection of the tumor cells after transfer into animals. In both cases, they also found rejections of mixtures of the Il-1 producing cells with the parent line tumor.

Biologal Charactristics of Il-1

Interleukin-1 (Il-1) is the term for two polypeptides (Il-1a and Il-1b) that possess a wide spectrum of inflammatory, metabolic, physiological, haematopoietic and immunological activities. Il-1 is synthesized by leukocytic as well as nonleukocytic cells (fibroblasts, endothelial, epithelial, dendritic and microglial cells and astrocytes) (32). The effects of Il-1 are not restricted to leukocytes but are manifested in nearly every tissue, where effects have been seen on e.g. fibroblasts (33), synovial cells (34), hypothalamic cells (30) and muscle cells (35). The first translation product of Il-1 is the pro-Il-1 31 kDa precursor; sequence analysis of the Il-1a and Il-1b precursors revealed that they do not contain a conventional N-terminal hydrophobic signal sequence (36, 37). The localization of cell associated Il-1 is almost entirely cytoplasmic, not in ER, Golgi or plasma membrane fraction (38,39). The half life of cell-associated Il-1a in monocytes is 15 hours, whereas that of Il-1b is 2.5 hours (40). The protein involved in processing of Il-la belongs to the family of calpain proteases (41,42), whereas Il-1b is cleaved by an aspartate specific protease (43,44).

Macrophages contain 10× more Il-1b (34) than Il-1a (34)' whereas endothelial cells and T-lymphocytes accumulate more Il-1a than Il-1b (45).

Two different cDNA sequences encoding hIl-la have been isolated (36,46,47). They differ in two nucleotides, of which one is in the protein coding region. This mutation leads to an amino acid polymorphism at position 114 of the precursor protein (which is aminoacid 2 of the mature protein), where either an Ala or a Ser is encoded (47). Both the precursors and the mature protein proved to have full biological activity (47), and seem therefore to represent a natural polymorphism.

Il-1 is a key regulator of inflammatory responses. Inflammation results in attraction of cells of the immune system, causing a cascade of reactions, including the production of other cytokines by the attracted immune cells, resulting in carcinolysis. Therefore, gene therapy of cancer may be achieved by production of human Il-1 by tumor cells. Secretion of Il-1 has to be local secretion by the tumor cells, to prevent systemic side effects. Therefore, in vivo gene transfer of the Il-1a gene or cDNA encoding pre-cursor IL-1a protein is needed.

The reasons for using in vivo gene transfer of Il-1a precursor by means of recombinant adenoviruses are: Il-1a is normally produced by a wide variety of cells the pre-cursor form of Il-1a, which is not secreted as such, is bioactive (36,48), in contrast to the pre-cursor of Il-1b, which has been reported to be biologically inactive see e.g. (49–51) or has strongly reduced activity (51). Both precursor proteins stay intra-cellularly. However, when gene therapy is combined with e.g. radiotherapy, chemotherapy or other ways of cancer gene therapy such as suicide gene transfer, and when tumor cells harboring the Il-1a precursor cDNA are lysed as a consequence of those treatments, this will result in release of bioactive Il-1a and may thus have a synergistic effect to these treatments Il-1a can induce the secretion of Il-1b by macrophages and monocytes, thus increasing the total amount of Il-1 at the site of the tumor adenovirus has proven to be able to efficiently deliver genes to somatic cells in vivo. Therefore, recombinant adenovirus is the vehicle of choice to transfer the Il-1a precursor cDNA into tumor cells in vivo.

BRIEF DESCRIPTION OF THE FIGURES

FIG. 1 shows the nucleotide sequence of HSV-tk (SEQ ID NO:3).

FIG. 3a shows preparation of pSad by digestion of pMLP.nls.lacZ with EcoRI and religation.

FIG. 3b shows the final steps of construction of pMLP.TK. The components are as follows. (1) MLPtpl major late promoter/tripartite leader sequences of Ad2; (2) SV40 poly(A) signal; (3) adenovirus-5 sequences; (4) HSV-TK; (5) pBR322; (6) AMP.

FIG. 11a shows the effect on human U251 cells; FIG. 11b shows the effect on human D384 cells; FIG. 11c shows the effect on human LW5 cells; FIG. 11d shows the effects of IG.Ad.MLP.TK on rat 911 glioma cells; and FIG. 11e shows the effects of IG.Ad.CM-V.TK on rat 911 glioma cells.

FIGS. 14a–14j show the results of in vivo administration of adenovirus producing cells to experimental rat tumors.

On day one, L42 tumors were implanted subcutaneously in both flanks of Wag/Rij rats. The animals were divided into five groups (n=4). The five groups are as follows. (1) animals with only L42 tumors; (2) animals injected with non-infected 293 cells; (3) animals injected with 293 cells infected with IG.Ad.MLP.lacZ; (4) animals injected with 293 cells infected with IG.Ad.MLP.rIL-3; (5) animals injected with 293 cells infected with IG.Ad.MLP.hIL-1α. Only the left flank tumor was injected with treatments (2)-(5), first on day 10 and again on day 20.

Figures 14I, 14J:
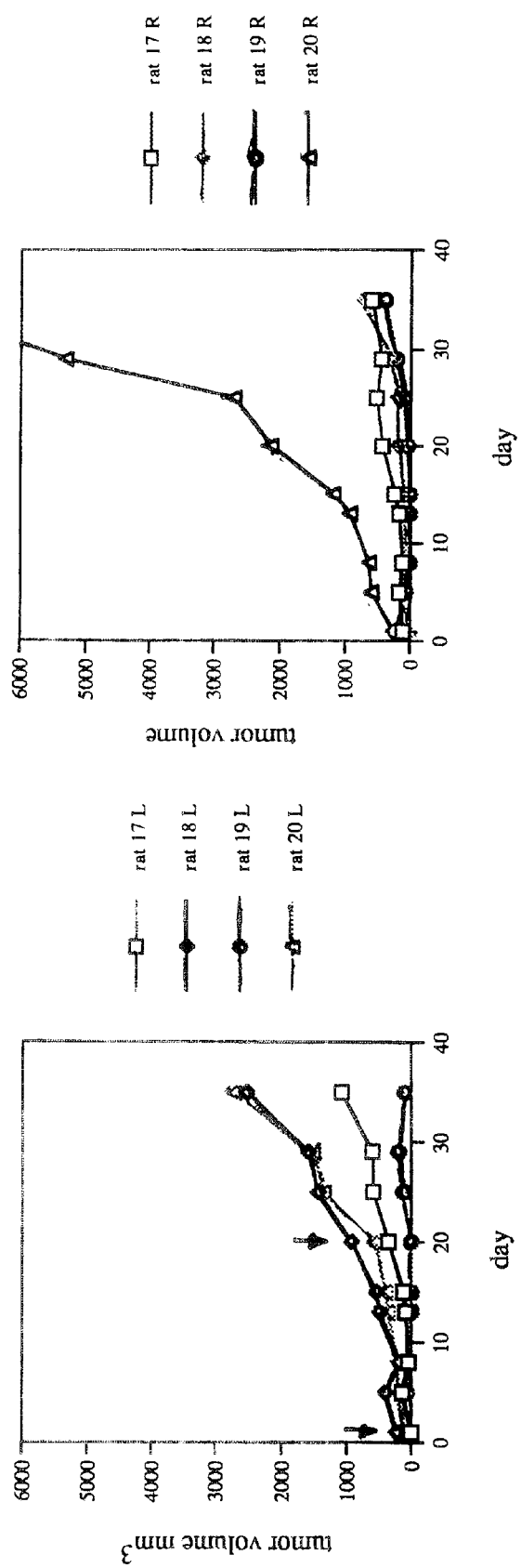

FIGS. 14a and 14b show the left and right tumors for individual rats injected with only L42 tumor. Individual rats are identified as follows: □, rat 1; ◇, rat 2; ○, rat 3; and Δ rat 4. FIGS. 14c and 14d show the left and right tumors for animals receiving L42 tumor and injected with 293 cells in the left flank tumors. Individual animals are identified as follows. □, rat 5; ◇, rat 6; ○, rat 7; and ▽, rat 8. FIGS. 14e and 14f show the effects of treatment on animals receiving L42 tumor and injected with 293 cells infected with Ad.M-LP.lacZ. Individual animals are identified as follows: □, rat 9, ◇, rat 10; ●, rat 11; and Δ, rat 12. FIGS. 14g and 14h show the effects of treatment on animals receiving L42 tumor and injected with 293 cells infected with Ad.MLP.IL-3. Individual animals are identified as follows: □, rat 13; ○, rat 14; +, rat 15; and ◇, rat 16. FIGS. 14i and 14j show the effects of treatment on animals receiving L42 tumor and injected with 293 cells infected with Ad.MLP.IL-1 in the left flank tumors. Individual animals are identified as follows. □, rat 17; ◇, rat 18; ○, rat 19, and Δ20.

EXPERIMENTAL

EXAMPLE 1

Treatment of Cancer with Recombinant Adenovirus Harboring the HSV-TK Gene, Followed by Systemic Injection of Ganciclovir 1.1 Cloning of HSV-TK Sequences a) The TK-cDNA is pHA 140 plasmid derived, from Berns, A'dam.

The TK gene was amplified by Polymerase Chain reaction (PCR).

enzyme: Deep Vent (New England Biolabs), 1 unit, 30 cycles of 1 min. 90° C., 1 min. 60° C. en 2 minutes 72° C.

primers: upstream:
5'-CTCTAAGCTTGAAGCGCGCGTATGGCTTCG-3'
(SEQ ID NO:1)

downstream:
5'-ACACTCTAGAGTGTTTCAGTTAGCCTCC-3'
(SEQ ID NO:2)

The resulting PCR fragment was digested with BamHI and HindIII and ligated into pSP65 digested with the same restriction enzymes. The resulting clone was named pSP65.TK.

b) Sequencing of the cloned HSV-TK-gene, (1130 base pairs): The TK gene of pSP65.TK was sequenced. The HSV-TK sequence is described by McKnight (56).

As compared to this sequence 3 differences exist: on position 16 (G instead of T), 126 (T instead of C), 267 (A instead of G)

The HSV-TK sequence, which is depicted in the FIG. 1, is identical with the original one (that is in pHA140), indicating that no artefacts were introduced by the PCR and cloning procedures.

```
ATGGCTTCGTACCCCTGCCATCAGCACGCGTCTGCGTTCGACCAGGCTGCGCGTTCTCG

CGGCCATAGCAACCGACGTACGGCGTTGCGCCCTCGCCGGCAGCAAGAAGCCACGGAAG

TCCGCCTGGAGCAGAAAATGCCCACGCTACTGCGGGTTTATATAGACGGTCCCCACGGG

ATGGGGAAAACCACCACCACGCAACTGCTGGTGGCCCTGGGTTCGCGCGACGATATCGT

CTACGTACCCGAGCCGATGACTTACTGGCAGGTGCTGGGGGCTTCCGAGACAATCGCGA

ACATCTACACCACACAACACCGCCTCGACCAGGGTGAGATATCGGCCGGGGACGCGGCG

GTGGTAATGACAAGCGCCCAGATAACAATGGGCATGCCTTATGCCGTGACCGACGCCGT

TCTGGCTCCTCATATCGGGGGGAGGCTGGGAGCTCACATGCCCCGCCCCCGGCCCTCA

CCCTCATCTTCGACCGCCATCCCATCGCCGCCCTCCTGTGCTACCCGGCCGCGCGATAC

CTTATGGGCAGCATGACCCCCCAGGCCGTGCTGGCGTTCGTGGCCCTCATCCCGCCGAC

CTTGCCCGGCACAAACATCGTGTTGGGGGCCCTTCCGGAGGACAGACACATCGACCGCC

TGGCCAAACGCCAGCGCCCCGGCGAGCGGCTTGACCTGGCTATGCTGGCCGCGATTCGC

CGCGTTTACGGGCTGCTTGCCAATACGGTGCGGTATCTGCAGGGCGGCGGGTCGTGGCG

GGAGGATTGGGGACAGCTTTCGGGGACGGCCGTGCCGCCCCAGGGTGCCGAGCCCCAGA

GCAACGCGGGCCCAGCACCCCATATCGGGGACACGTTATTTACCCTGTTTCGGGCCCCC

GAGTTGCTGGCCCCCAACGGCGACCTGTACAACGTGTTTGCCTGGGCCTTGGACGTCTT

GGCCAAACGCCTCCGTCCCATGCACGTCTTTATCCTGGATTACGACCAATCGCCCGCCG
```

```
                    -continued
GCTGCCGGGACGCCCTGCTGCAACTTACCTCCGGGATGATCCAGACCCACGTCACCACC

CCAGGCTCCATACCGACGATCTGCGACCTGGCGCGCACGTTTGCCCGGGAGATGGGGGA

GGCTAACTGA
```

FIG. 1 (SEQ ID NO:3) Nucleotide sequence of HSV-TK.

Figure 2:
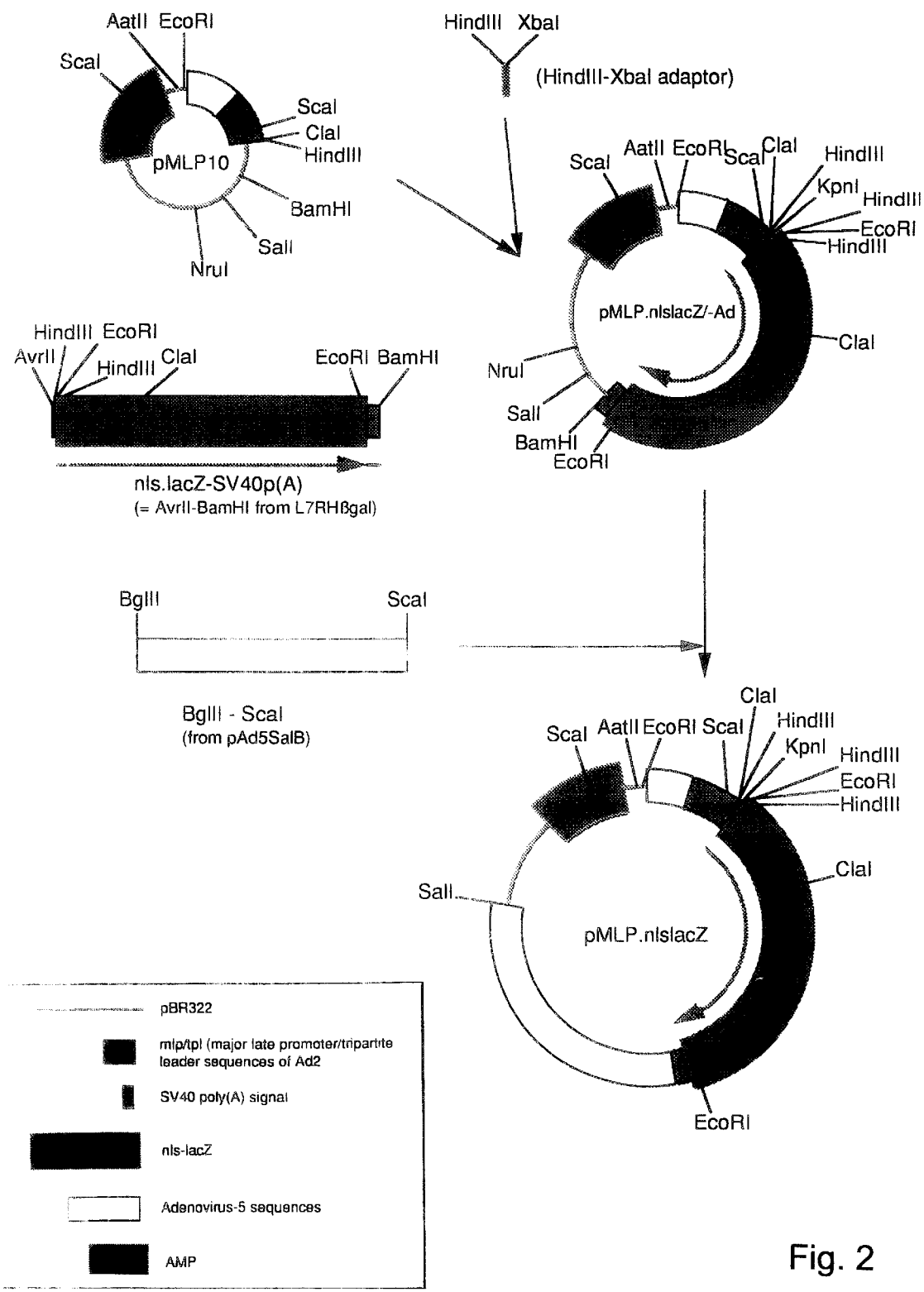
FIG. 2 shows construction of pMLP.nlslacZ. The components of the construct shown are as follows. (1) nls-lacZ; (2) AMP; (3) MLP/tpl (major late promoter/tripartite leader sequences of Ad2; (4) SV40 poly(A) signal; (5) adenovirus-5 sequences; (6) pBR322.

1.2 Construction of pMLP.nls.lacZ (FIG. 2).

pMLP.nls.lacZ was constructed according to the scheme presented in FIG. 2.

pMLP10 (53) was digested with HindIII and BamHI. nlslacZ was excised from L7RHαgal (54) with AvrII and BamHI andligated, together with a HindIII-XbaI linker sequence, into pMLP10 that was digested with HindIII and BamHI. The new construct was named pMLP.nls.lacZ/-Ad.

The HindIII-XbaI linker sequence was made by hybridization of the following oligonucleotides:

```
LK1 5'-AGCTTGAATTCCCGGGTACCT-3' (SEQ ID NO:4) linker
LK2 5'-CTAGAGGTACCCGGGAATTCA-3' (SEQ ID NO:5) linker
```

The BglII-ScaI (nt. 3328–6092) from adenovirus type 5 was ligated into pMLP.nls.lacZ/-Ad after digestion with BamHI and NruI. The resulting construct was pMLP-.nls.lacZ.

Figure 3A:
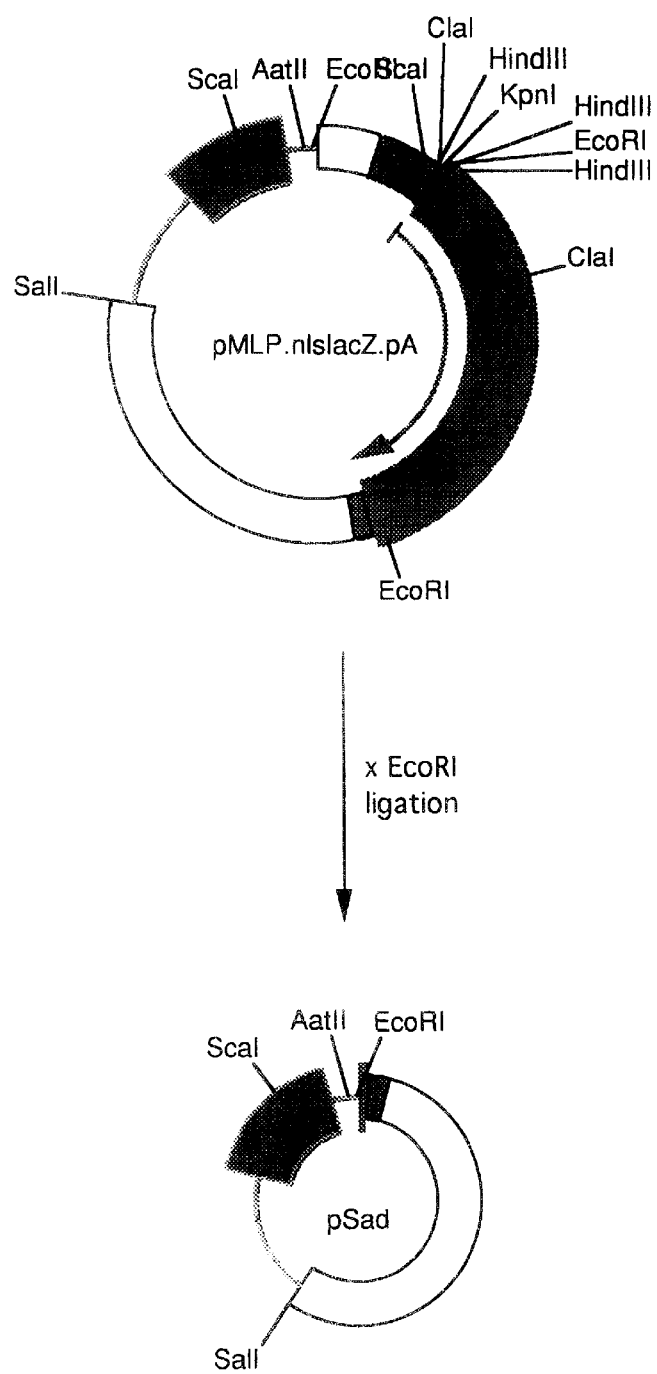
FIGS. 3a and 3b show construction of pMLP.TK.
Figure 3B:
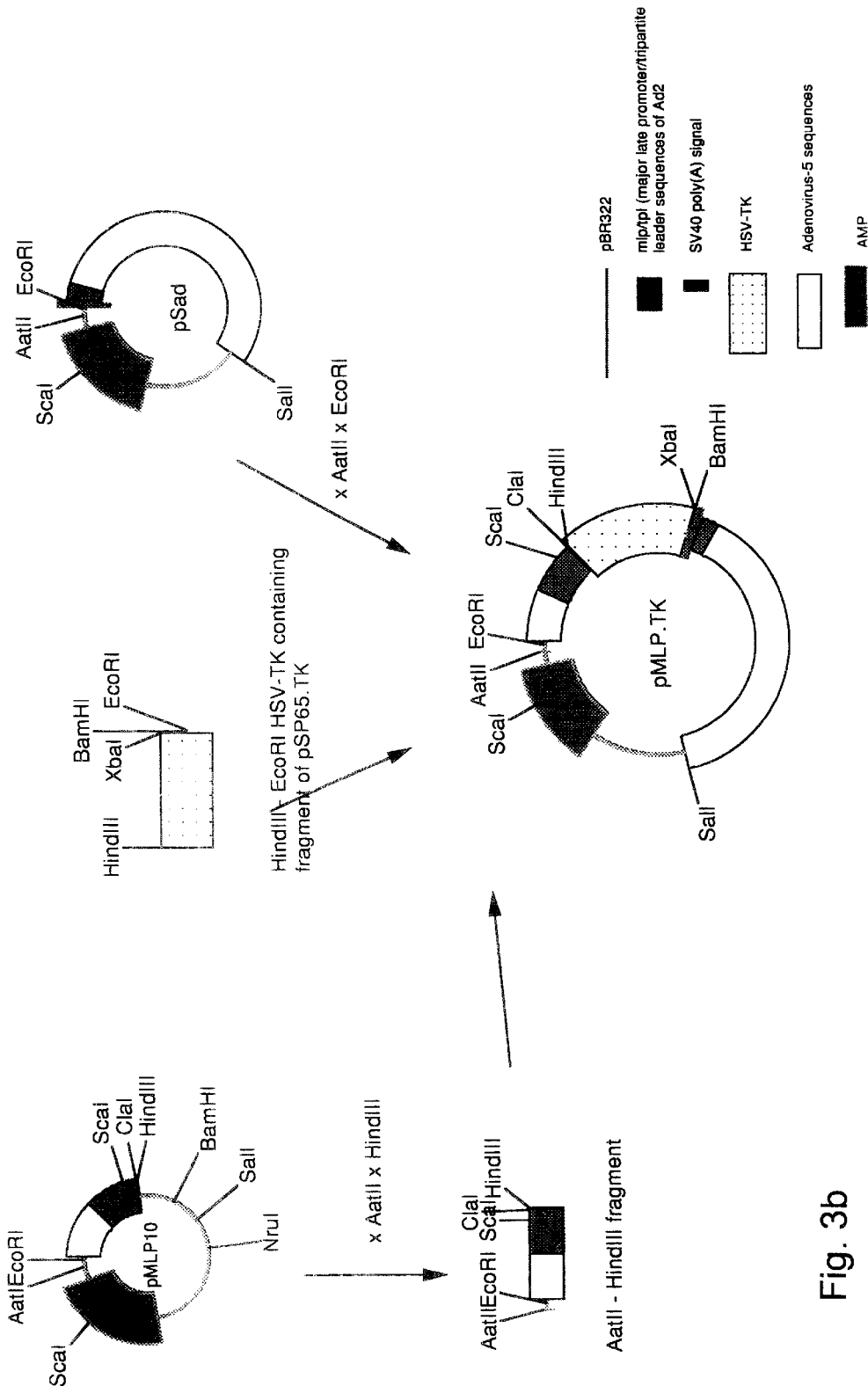

1.3 Construction of pMLP.TK (FIGS. 3a and 3b).

First, an intermediate contruct was generated that the adenovirus type 5 sequences from nt. 3328–6092. This clone named pSad, was made by digestion of pMLP.nls.lacZ with EcoRI and religation.

pMLP.TK was made by ligating:

AatII-HindIII fragment of pMLP10 (containing the left ITR and the MLP promoter sequences)

HindIII-EcoRI HSV-TK containing fragment of pSP65.TK, AatII-EcoRI digested pSad.

The resulting clone was designated pMLP.TK.

Integrity of this construct was assessed by restriction enzyme analysis, sequence analysis of the boundaries between TK and the MLP promoter, between TK and the adenovirus fragment (nt. 3328–6092 of Ad5), including the SV40 poly(A) signal.

Transfection into TK negative osteosarcoma (143) cells chances HAT and ganciclovir sensitivity, indicating that the HSV-TK gene is functional.

Figure 4:
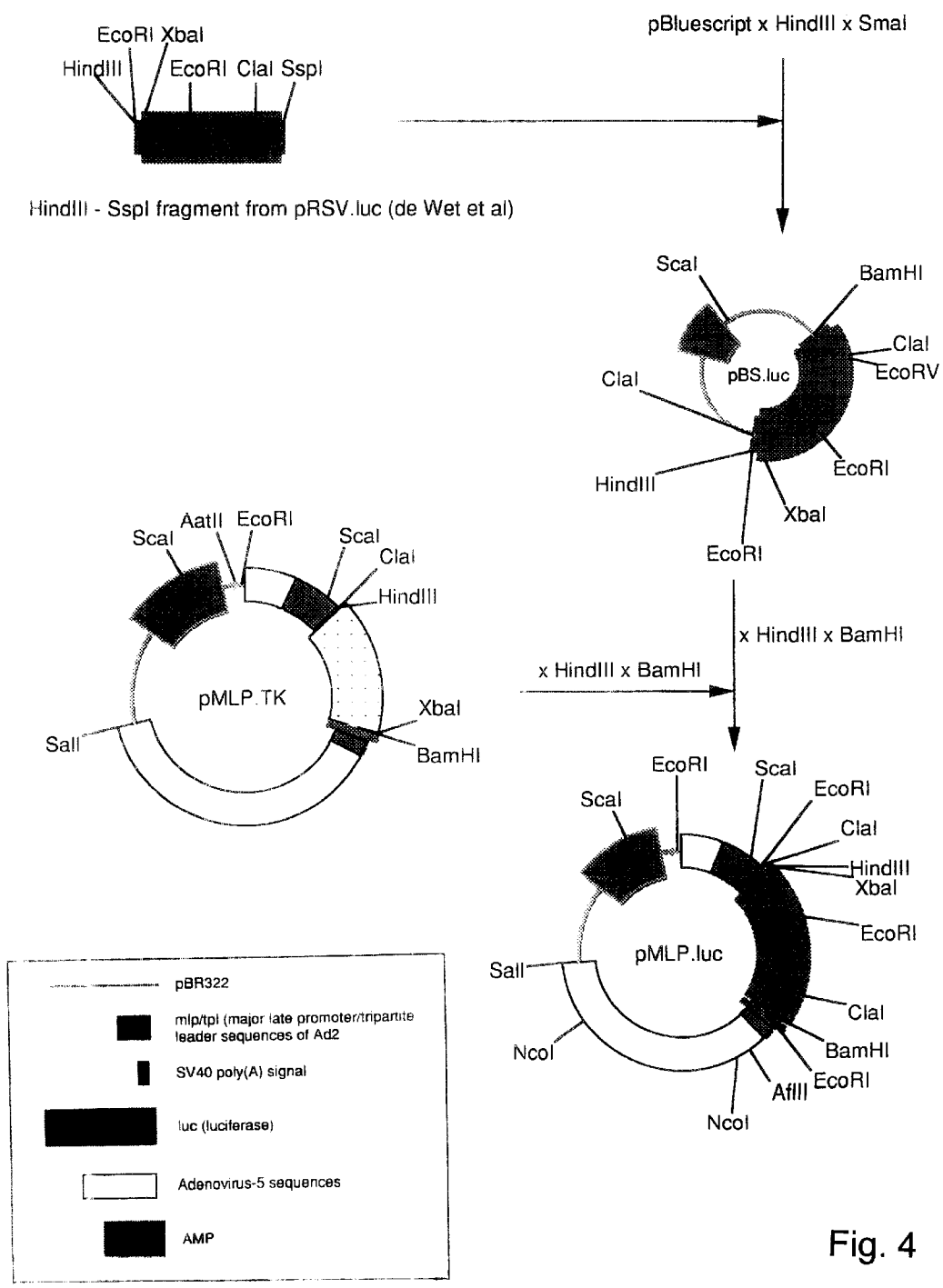
FIG. 4 shows construction of pMLP.luc. The components are as follows. (1) luc (luciferase); (2) AMP; (3) MLP/tpl (major late promoter/tripartite leader sequences of Ad2; (4) SV40 poly(A) signal; (5) adenovirus-5 sequences; (6) pBR322.

1.4 Construction of pMLP.luc (FIG. 4)

A similar adenovirus construct containing the firefly luciferase gene (luc) under the control of the MLP (pMLP.luc) was made. The luc was isolated from pRSV.luc (55) with restriction enzymes HindIII and SspI and ligated into pBluescript (Stratagene) which was digested with HindIII and SmaI. The resulting clone was named pBS.luc.

HSV-TK in pMLP.TK was exchanged by luc from pBS.luc by digestion and ligation of the respective HindIII-BamHI fragments.

Figure 5:
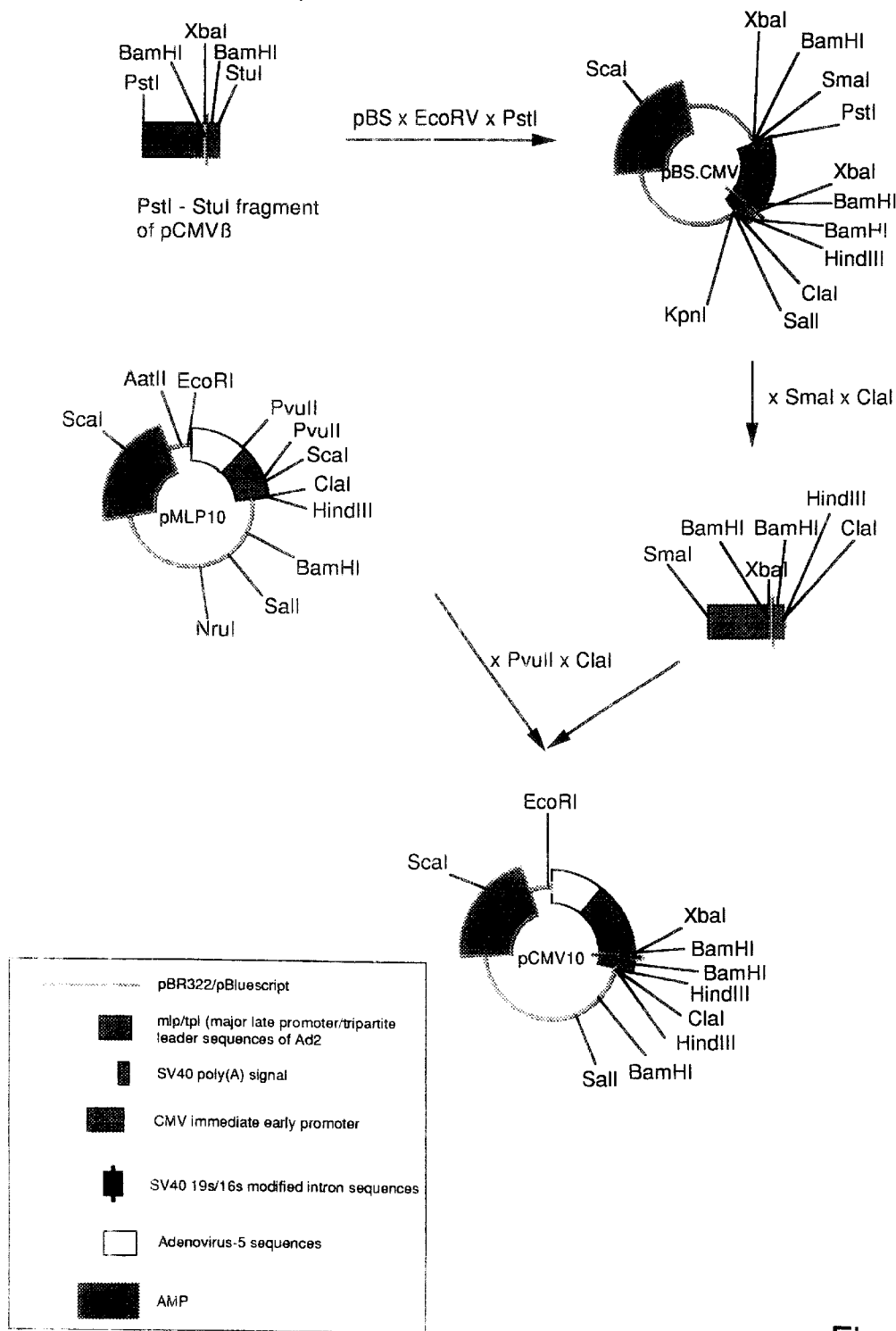
FIG. 5 shows construction of pCMV. 10. The components are as follows. (1) SV40 19s/16s modified intron sequences; (2) AMP; (3) MLP/tpl (major late promoter/tripartite leader sequences of Ad2; (4) SV40 poly(A) signal; (5) adenovirus-5 sequences; (6) pBR322/pBluescript; (7) CMV immediate early promoter.
Figure 6:
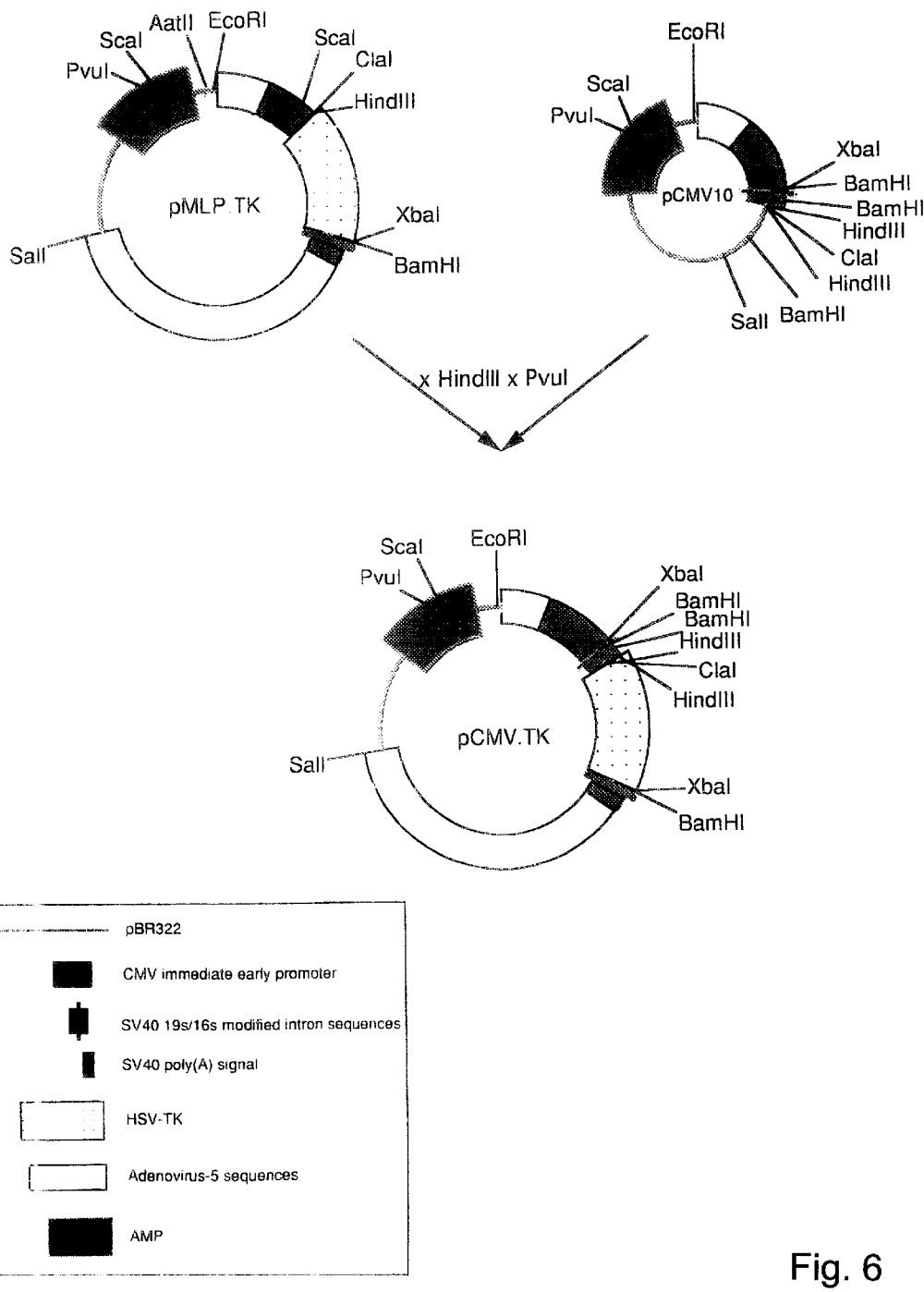
FIG. 6 shows construction of pCMV.TK. The components are as follows. (1) HSV-TK; (2) AMP; (3) SV40 19s/16s modified intron sequences; (4) SV40 poly(A) signal; (5) adenovirus-5 sequences; (6) pBR322; (7) CMV immediate early promoter.
Figure 7:
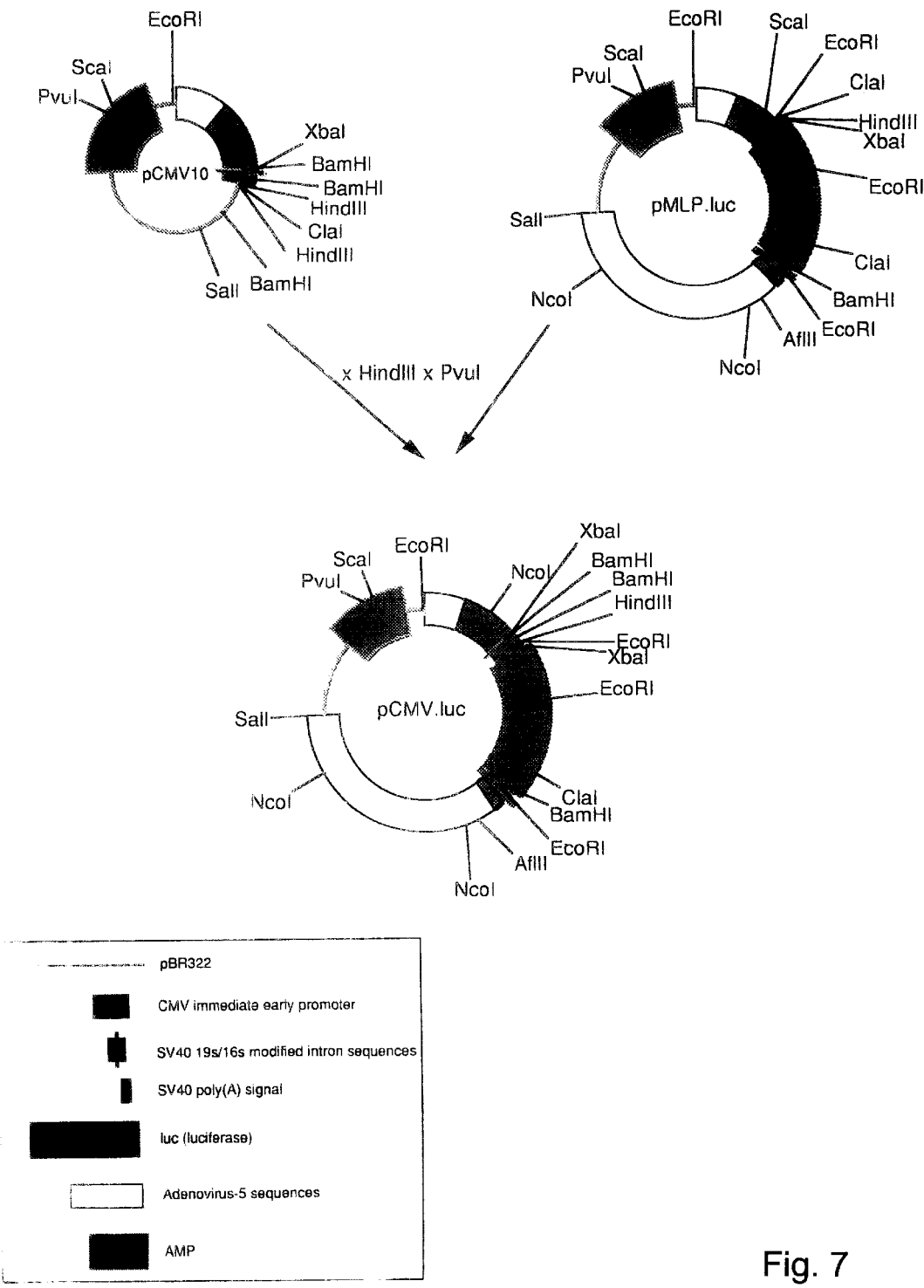
FIG. 7 shows construction of pCMV.luc. The components are as follows. (1) luc (luciferase); (2) AMP; (3) SV40 19s/16s modified intron sequences; (4) SV40 poly(A) signal; (5) adenovirus-5 sequences; (6) pBR322; (7) CMV immediate early promoter.

1.5 Construction of pCMV.TK and pCMV.luc (FIGS. 5, 6 and 7).

As the activity of the Major Late Promoter (MLP) is relatively low, additional recombinant adenoviruses were generated in which the recombinant gene (HSV-TK, luc, etc.) is driven by the Cyto-Megalovirus (CMV) immediate early promoter, which is a strong promoter. A new basic construct containing the CMV promoter was made according to the scheme presented in FIG. 5 The CMV promoter together with SV40 derived intron sequences downstream of it, were derived from pCMVα (Clontech) by digestion with PstI and StuI, and ligated into pBluescript (Stratagene) digested with PstI and EcoRV, resulting in pBS.CMV.

The CMV promoter containing fragment was excised from PBS.CMV using SmaI and ClaI and ligated into pMLP10 that was digested with PvuII and ClaI. The new clone was named pCMV.10.

PCMV.TK and pCMV.luc were made by ligating the HindIII-PvuI fragment of pCMV.10 into PMLP.TK and pMLP.luc, respectively, that were digested with the same restriction enzymes.

1.6 Generation of Recombinant Adenoviruses

The adenoviruses IG.Ad.MLP.TK, IG.Ad.CMV.TK, IG.Ad.MLP.nls.lacZ, IG.Ad.MLP.luc and IG.Ad.CMV.luc, were generated by recombination in 293 cells & plaque purification. The procedure is schematically presented in FIG. 8. Recombinant adenoviruses were prepared by co-transfection of adenoviral constructs (pMLP.TK, pCMV.TK, pMLP.luc and pCMV.luc) and the large ClaI fragment of wild-type human adenovirus 5. Two days after co-transfection, the cells were harvested and subjected to three cycles of freezing/thawing. The supernatant was applied to fresh 293 cells and overlaid with agar the next day. 6 days after infection, a second agar overlay was performed, using agar containing neutral red to visualize plaques. Plaques were picked, put in 200 ml. culture medium, and 20 ml of this virus suspension was added to 293 cells. At full CPE, the lysed cells were harvested and assayed for the presence of HSV.TK (Southern blotting) or luciferase (by assessing luciferase activity). Positive plaques underwent a second plaque purification, and were assayed similarly. One positive plaque was used for making a virus master stock by inoculating 293 cells in a 75 $cm^2$ flask with the plaque purified material. 4 ml. of the virus master stock was used to inoculate 20 175 $cm^2$ flasks containing 293 cells. After 72 hours, when full CPE was seen, the 293 cells were collected and virus was purified on a CsCl density gradient and dialyzed according to routine procedures (56).

The identity of the resulting viruses was checked by restriction enzyme analysis and Southern blotting. All these viruses contain a wild-type E3 region.

1.7 Use of IG.Ad.CMV.TK for Treatment of Rat Mesothelioma

Fisher 344 rats, (n=16), weighing 250–360 grams, were anesthesized with ether. A small opening was made between the 8th and the 9th rib, at the right side. $1 \times 10^5$ II45 rat mesothelioma cells in 200 µl of PBS were injected intrathoracically. The needle was retracted and the intercostal opening was closed by 4×0 sutures atraumatic. The skin wound was closed with 9 mm autoclips. One day after tumor cell implantation, the same procedure and location was used to inject recombinant adenovirus. $7 \times 10^9$ infection units of IG.Ad.CMV.TK in 200 µl of PBS (n=8) or 200 µl of PBS (n=8) were injected. Twenty-four hours later, a 13-days treatment of GCV (50 mg/kg/day) or PBS delivered IP was started twice a day. The animals were divided in four groups: 1- injected with PBS/treatment with PBS (n=4), 2- PBS/GCV (n=4), 3- IG.Ad.CMV.TK/PBS (n=4), 4- IG.Ad.CMV.TK/GCV (n=4). At day 14, the rats were sacrified, and inspected for the spresence of macroscopic tumor infiltration intrathoracically. The thoracic contents (lungs, heart, mediastinum, trachea, and the diafragma) including possible tumors were weighed.

| Results | Macroscopical tumor growth | | | no macrosc. tumor |
|---|---|---|---|---|
| | 1 | 2 | 3 | 4 |
| Treatment | PBS/PBS | IG.Ad.CMV. TK/PBS | PBS/GCV | IG.Ad.CMV. TK/GCV |
| weight (g) (x ± SD) | 8.45 ± 1.47 | 7.9 ± 0.8 | 6.62 ± 2.05 | 4.38 ± 0.48 |

Conclusion.

Treatment of rats with mesothelioma by administration of IG.Ad.CMV.TK followed by treatment with GCV results in killing of tumor cells.

Figure 9:
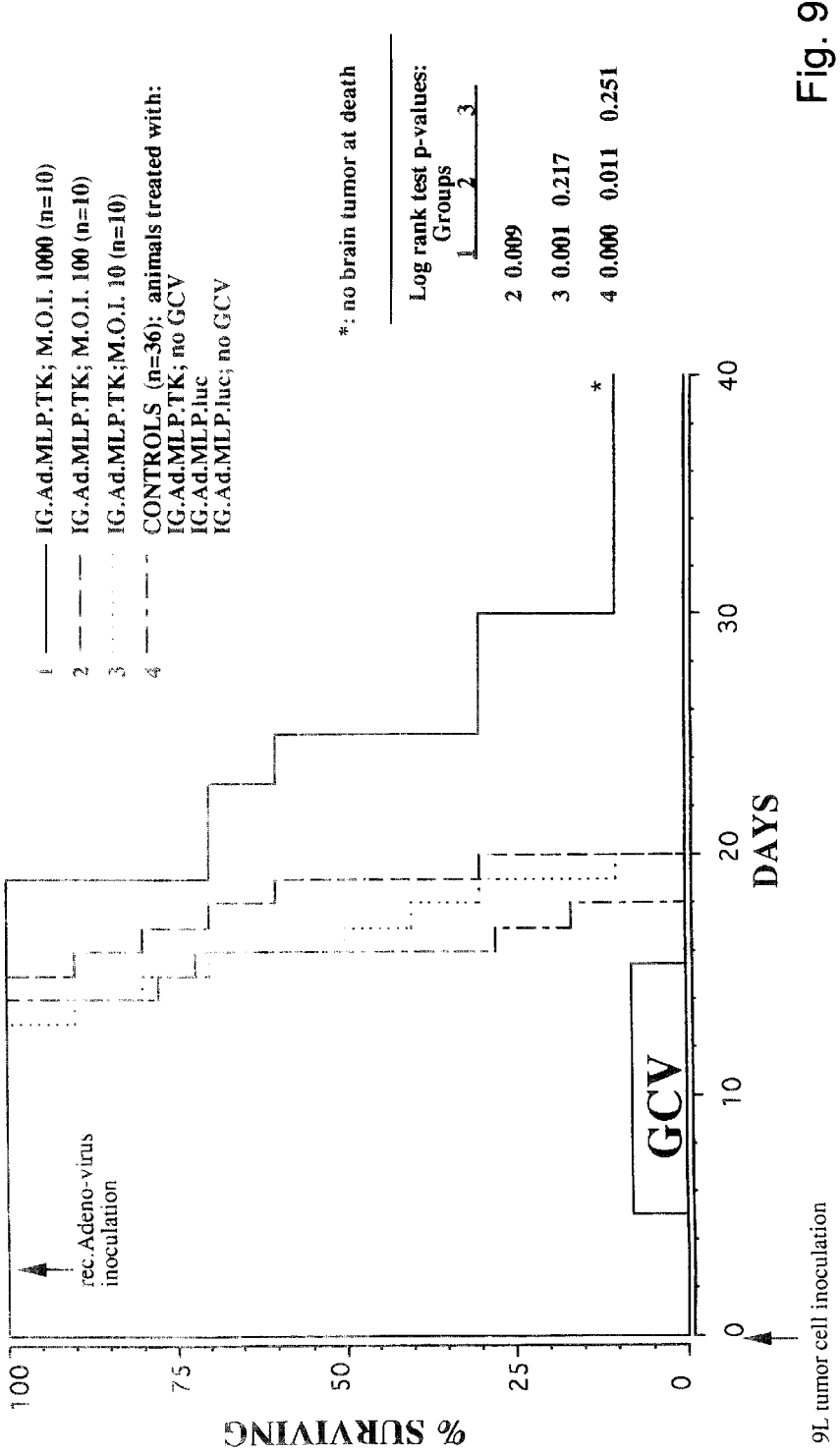
FIG. 9 shows a Kaplan-Meier survival curve in rats with brain tumors treated with single doses of recombinant adenovirus and subsequent GCV therapy. There are three test groups as follows. (1) IG.Ad.MLP.TK; M.O.I. 1000 (n=10); (2) IG.AdMLP.TK; M.O.I. 100 (n=10); (3) IG.Ad.MLPTK; M.O.I. 10 (n=10). There were also three control groups (n=36 total) shown at (4). The three control groups included IG.Ad.MLP.TK (no GCV); IG.Ad.MLP.luc; and IG.Ad.M-LP.luc (no GCV). * represents that no brain tumor death occurred in some mice of this group. The p-values are as follows: groups one vs. two, 0.009; groups one vs. three, 0.001; groups three vs. two, 0.217, groups four vs. groups one, 0.000; groups four vs. groups two, 0.011; and group four vs. three, 0.251.

1.8 Treatment of Rat Braintumors by Intratumoral Injection of Adeno-TK Followed by Intraperitoneal Ganciclovir Injections A rat (9L glioma) model (57) was used to study the effect of IG.Ad.MLP.TK and GCV in a malignant brain tumor. Fischer 344 rats, weighing 200–400 grams, were randomised, anesthesized with ether and placed in a stereotaxic frame. A burr hole was made 1 mm in front of the bregma and 2 mm lateral of the midline. $4 \times 10^4$ 9L rat-gliosarcoma cells in 1 $\mu$l of Hank's buffered saline were injected with a microliter syringe (27 gauge needle; Hamilton) into the left forebrain at a depth of 4 mm below the skull. The cells were injected over a period of 2 minutes. The needle was slowly retracted and the burr hole was closed with bonewax (Braun). The skin was closed with 9 mm autoclips. The same procedure and coordinates were subsequently used to inject recombinant adenovirus. A volume of 10 $\mu$l was infused over 5 minutes along the needle track. 3 days after tumor cell implantation different amounts of IG.Ad.MLP.TK or IG.Ad.MLP.luc as control were injected at the same site in 8 different groups of rats; $5.10^8$ (n=6), $10^8$ (n=16), $10^7$ (n=10) and $10^6$ (n=10) pfu's of IG.Ad.MLP.TK and $5.10^8$ (n=7), $10^8$ (n=12) pfu's of IG.Ad-.MLP.luc. It was calculated that the different groups treated at day 3 with IG.Ad.MLP.TK and IG.Ad.MLP.luc were infected with an m.o.i. of approximately 5000, 1000, 100, 10 and 5000, 1000 respectively, by assuming a population of $10^5$ tumor cells at the respective time points of virus inoculation, based on a cell doubling time of 18–20 hours (57). Fourty eight hours after the injection of the virus, the rats received twice a day 15 mg/kg ganciclovir (Syntex) or PBS intraperitoneally for ten days. From all rats that died the brain tumors were dissected and weighed. The results are graphically presented in FIG. 9. From this figure we conclude that rats treated with IG.Ad.MLP.TK at an m.o.i of 5000 and 1000 showed significantly prolonged survival time as compared to the rats given IG.Ad.MLP.luc or IG.Ad.M-LP.TK without GCV treatment (log rank test, p<0.01). Two animals in the group treated with m.o.i 5000 and one animal in the group treated with m.o.i 1000 died of superficial leptomeningeal tumor which was caused by spill of tumor cells through the burr hole. Intracerebral tumors were not present in these rats. In addition, rats treated with IG.Ad. MLP.TK at an m.o.i. of 100 survived 18.3 days on the average (FIG. 9) as compared to 15.7 days for the control group. The survival time in this treated group was significantly prolonged as compared to controls (log rank test, p<0.05). Survival of rats treated with $10^6$ pfu's (m.o.i. of 10) was not significantly different from that of controls (log rank test, p>0.05).

1.9 Treatment of Leptomeningial Metastasis with IG.Ad.M-LP.TK and IG.Ad.CMV.TK

Leptomeningeal metastases occurs in 8% of cancer patients. They most frequently originate from tumors of the lung, breast and melanoma (58). In order to study whether Ad.TK treatment is effective for treatment of leptomeningial metastasis, the 9L Fisher-rat model was used. $4 \times 10^4$ 9L tumor cells were injected into the liquor cerebrospinalis of the IVth. ventricle on day 0, followed by infusion of $10^9$ pfu of recombinant adenovirus (either IG.Ad.MLP.TK or IG.Ad.CMV.TK) on day 3 into the same site. Animals were treated with ganciclovir for 14 days, the treatment starting on day 5. Animals injected with tumor cells only and treated with GCV or injected with virus only served as controls. The animals were observed daily. When symptoms of disease, such as paralysis, were apparent the animals were sacrificed.

Figure 10:
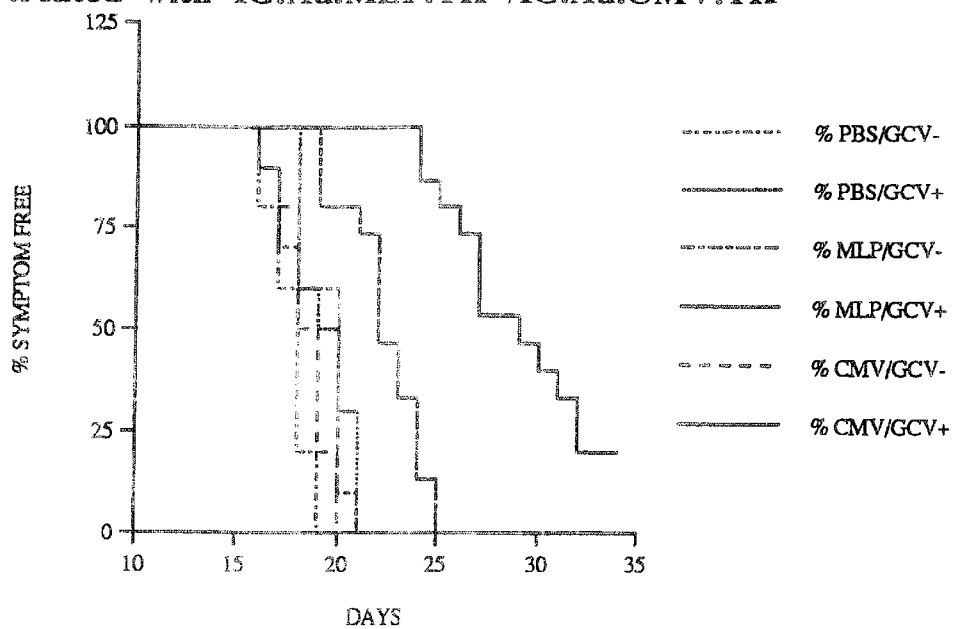
FIG. 10 shows the symptom free period in rats with lepto-meningeal metastasis treated with IG.Ad.MLP.TK/ IG.Ad.CMV.TK. The results are indicated on the graph as follows. (1) PBS/GCV−; (2) PBS/GCV+; (3) MLP/GCV−; (4) MLP/GCV+; (5) CMV/GCV−; (6) CMV/GCV+.
Figure 11A:
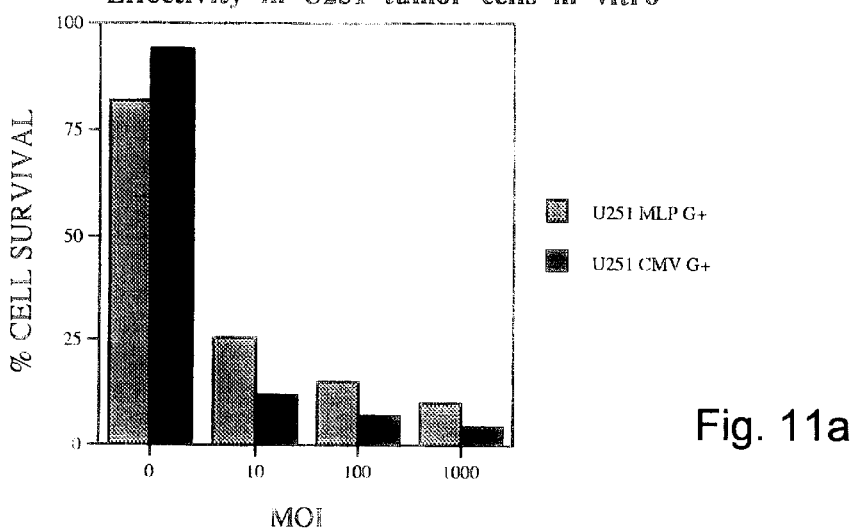
FIGS. 11a–11e show anti-tumor activity of IG.Ad.M-LP.TK and IG.Ad.CMV.TK and GCV treatment on human and rat glioma cells in vitro.
Figure 11B:
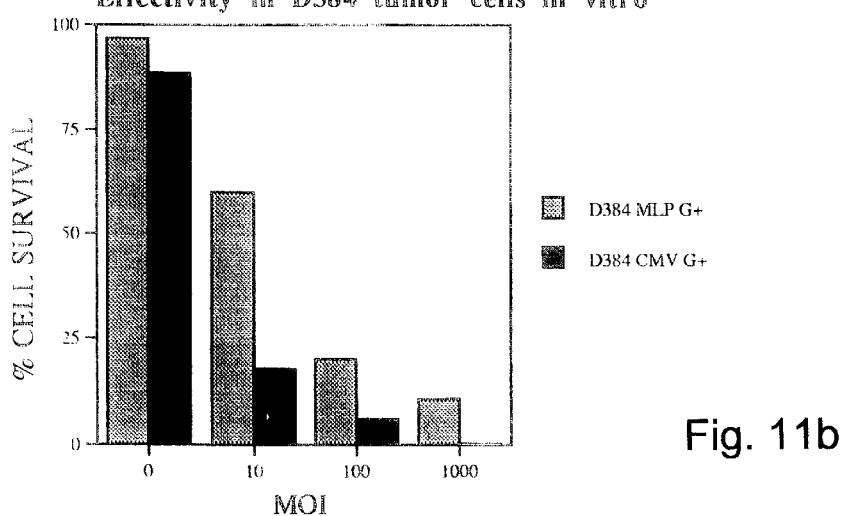
Figure 11C:
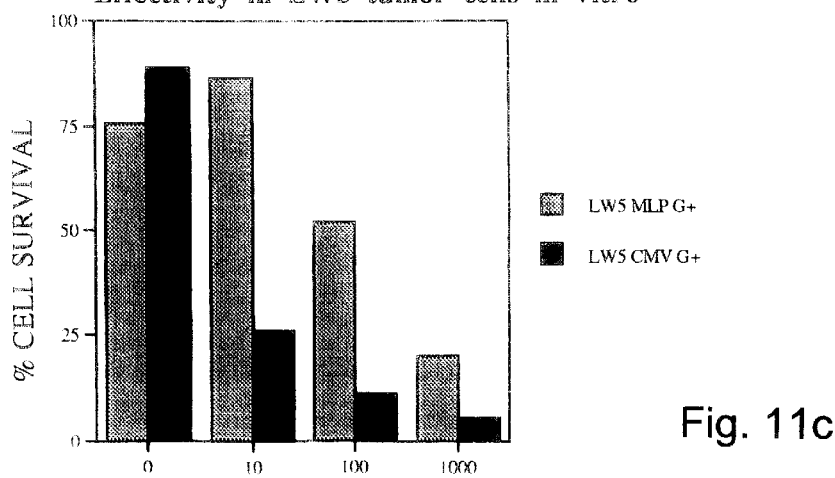
Figure 11D:
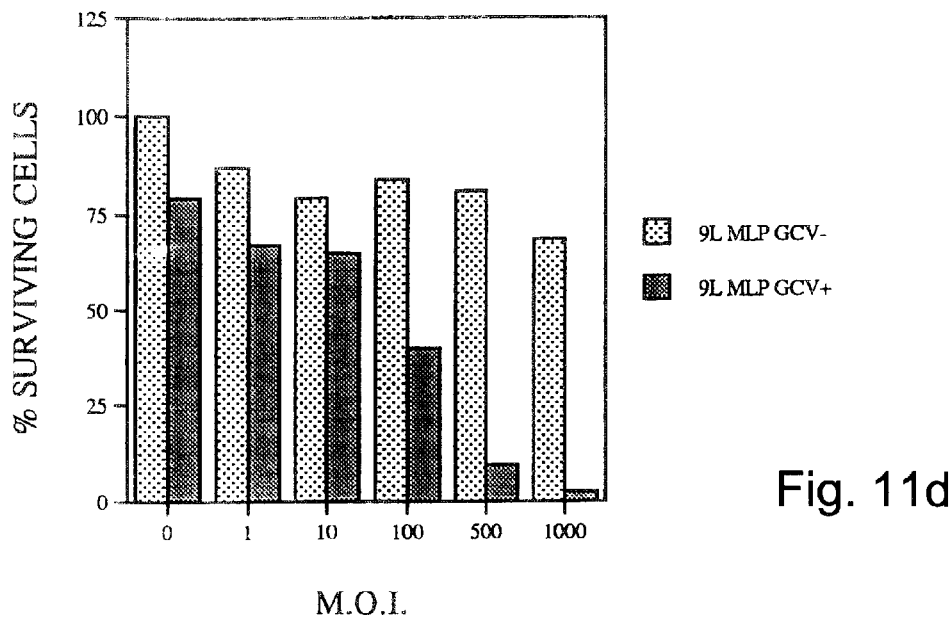
Figure 11E:
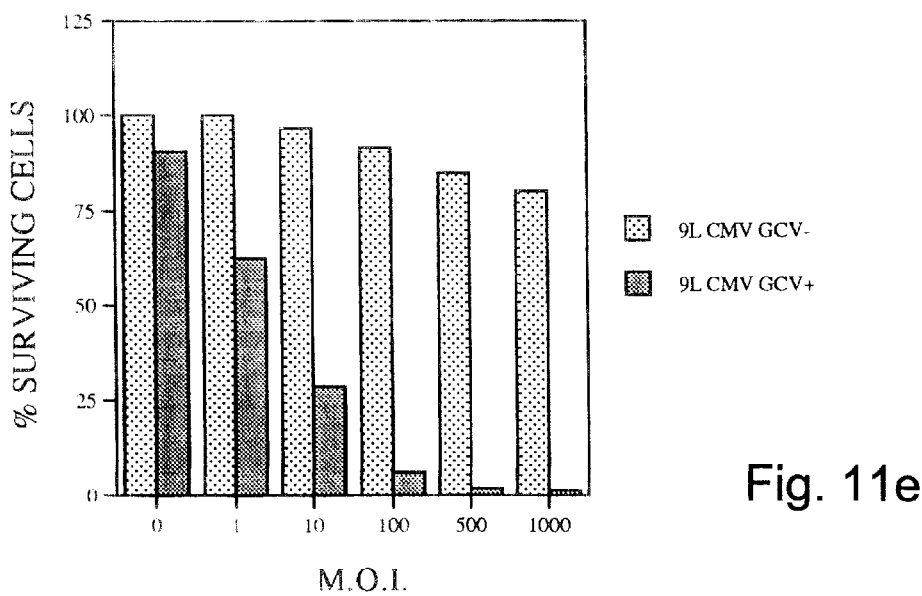

The results are presented in FIG. 10. From this experiment we conclude that treatment of leptomeningial metastasis with recombinant adenovirus a) leads to a significant prolonged disease free period and b) that IG.Ad.CMV.TK has a stronger anti-tumor effect than IG.Ad.MLP.TK, which is most likely explained by the strong CMV promoter activity and hence high levels of HSV-TK produced in transduced cells.

1.10 Toxicity of Recombinant Adenovirus in Normal Rat Brain

In order to assess the toxicity of IG.MLP.Ad.TK in normal brain tissue, a study has been performed according to the Table presented below. All groups consisted of three rats. A number of control groups have been included, of which one group of rats was treated with wild-type adenovirus type 5 as a 'positive' control for pathological side effects.

The treatment protocol was as follows:

Day 1: intracerebral injection of virus or control substances

Day 2—day 14: treatment of the animals with either ganciclovir or PBS twice daily Day 15: perfusion with 4% paraformaldehyde preparation of brain sections of 50 $\mu$m thickness using a vibratome stain sections with Hematoxilin, Phloxin and Saphran

| | intracerebral injection | treatment 14 days |
|---|---|---|
| 1. | PBS | 1 ml. PBS twice a day |
| 2. | PBS | 15 mg/kg GCV twice a day |
| 3. | 1 × $10^8$ pfu IG.Ad.MLP.TK | 1 ml. PBS twice a day |
| 4. | 1 × $10^8$ pfu IG.Ad.MLP.TK | 15 mg/kg GCV twice a day |
| 5. | 1 × $10^8$ pfu IG.Ad.MLP.TK + 1% wt Ad.5 | 1 ml. PBS twice a day |
| 6. | 1 × $10^8$ pfu IG.Ad.MLP.TK + 1% wt Ad.5 | 15 mg/kg GCV twice a day |
| 7. | 1 × $10^8$ pfu wt Ad5 | 1 ml. PBS twice a day |
| 8. | 1 × $10^8$ pfu wt Ad5 | 15 mg/kg GCV twice a day |

None of the rats died or showed gross clinical signs of disease during the experiment. Microscopic analysis of serial brain sections showed that only the needle tract was still recognizable by the presence of erythrocytes and macrophages containing iron, which indicate that some bleeding occured during injection. Clear pathological changes were only observed in the animals injected with $10^8$ pfu of wild-type adenovirus. Infiltrates of leukocytes, most likely lymphocytes, were observed in 10 serial sections, to a depth of approximately 0.5 mm This was observed in all three animals of this group. These pathological changes most likely reflect an immune response against cells infected by adenovirus. As the rat is non-permissive or semi-permissive, it might be that no replication of wild-type adenovirus occurred, but that because of expression of E1 genes other adenovirus genes are transactivated. Intracellular production of adenovirus antigens will elicit a cellular immune response. Such a pathological reaction has been described after intra-pulmonal administration of wild-type human adenovirus type 5 to mouse lungs in vivo. (8).

Lymphocytic infiltrates were not observed in any of the other treatment groups, including the animals that were injected with a mixture of IG.Ad.MLP.TK and 1% wtAd5. No differences were seen between sections of the control groups (groups 1, and those of the groups treated with recombinant viruses. 1 out of 3 rats of group displayed minor infiltrates in the corpus calosum, the reason of which is unknown.

The observation that none or at most minor histological deviations were observed is in contrast to changes reported by others (59).

It is not clear why there is such a marked difference between those data (59) and ours (note that we injected a 20× higher virus dose). Our explanation is that retainment of the E3 region in our virus prevents pathological side effects.

1.11 Anti-tumor Activity of IG.Ad.MLP.TK and IG.Ad.C-MV.TK and GCV Treatment on Human and Rat Glioma Cells In Vitro Rat 9 L glioma and human U251, D384 and LW5 glioma cells were infected with IG.Ad.MLP.TK and IG.Ad.CM-V.TK. Consequently, the infected cells were exposed to ganciclovir. Four days later, the cultures and the appropriate controls were trypsinized and counted to assess the number of surviving cells. The results are graphically presented in FIGS. 11a–11e. From this experiment we conclude that:

IG.Ad.CMV.TK is more effective than IG.Ad.MLP.TK (except for U251, where the difference is less pronounced), which is due to the strong CMV promoter present in IG.Ad.CMV.TK IG.Ad.CMV.TK is more toxic than IG.Ad.MLP.TK on human cells, but not on rat cells IG.Ad.CMV.TK and IG.Ad.MLP.TK are more effective in human cells than in rat cells 1.12 Planned use of IG.Ad.MLP.TK and IG.Ad.CMV.TK Recombinant adenoviruses are planned to be used in clinical studies for the treatment of at least gliomas, mesotheliomas and leptomeningeal metastases. For treatment of gliomas, the clinical protocol will consist of debulking of the tumor mass by surgery, followed by application of the virus to the wound bed. Another strategy envisages direct injection of purified IG.Ad.MLP.TK of IG.Ad.CMV.TK directly into the tumor.

Treatment proposal for leptomeningeal metastasis includes direct infusion of IG.Ad.MLP.TK or IG.Ad.CM-V.TK into a the liquor cerebrospinalis. Treatment of mesotheliomas will consist of administration of recombinant adenovirus to the pleural cavity.

We also include the administration of adenovirus producing cells lines, lethally irradiated or not, e.g. 293 cells that have been infected with IG.Ad.MLP.TK or IG.Ad.CMV.TK. Injection of Ad.TK producers will not only lead to in situ production of adenovirus particles, but these cells produce very high levels of thymidine kinase themselves. It is to be expected that such cells contribute significantly to the anti-tumor effect.

We do not restrict ourselves to glioma, mesothelioma and leptomengeal metastases, but in principle all solid tumors might be subject of treatment with suicide genes (viruses, packaging cells) and ganciclovir.

EXAMPLE 2

Cancer Gene Therapy with Recombinant Adenovirus Harboring Il-1α or Il-3 cDNA. 2.1 Isolation and cloning of hIL-1α precursor cDNA U937 cells (human monocyte cell line) were stimulated with lipopolysaccharides (PMA) to induce synthesis of IL-1 protein. RNA was extracted from the stimulated monocytes, reverse transcribed to make cDNA, which was subjected to PCR analysis using primers specific for human Il-1α. The sequence of the primers used for PCR analysis: forward plimer: 5'-CAGCAAAGAAGTCAAGATGGCC-3' (SEQ ID NO:6) reverse primer: 5'-GTGAGACTCCAGACCTACGCCTGG-3' (SEQ ID NO:7) The PCR product was ligated directly into pBluescript (Stratagene), which was pre-digested with SmaI. The resulting clone was named pBS.hIl-1α.

2.2 Method of Construction of Recombinant Adenovirus

Figure 12:
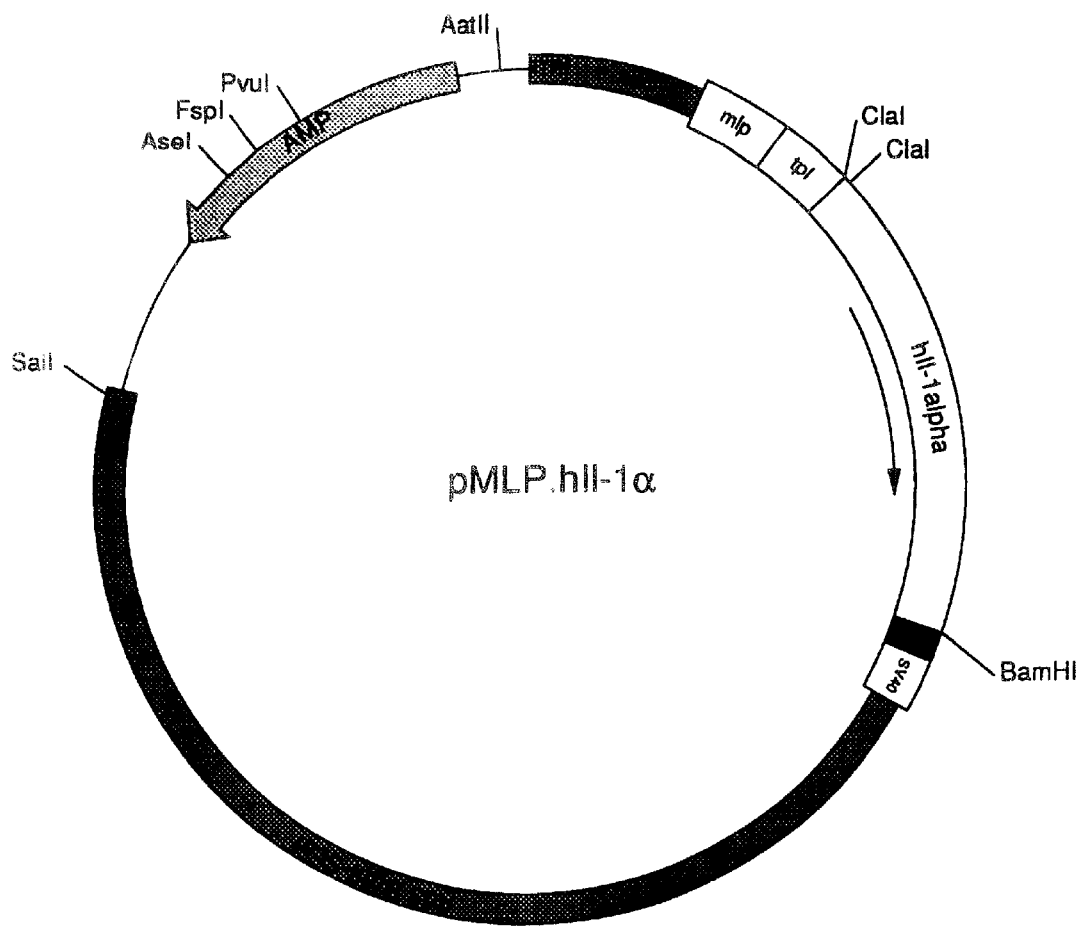
FIG. 12 shows the component of plasmid on pMLP.hIL-1α.

The first step in the construction of the virus was the replacement of HSV.TK in pMLP.TK by human Il-1α precursor cDNA. The 5' 430 bp (HindIII-EcoRI) were isolated from pBS.hIl-1α by partial digestion with HindIII and with EcoRI. The 3' part of the IL-1α precursor cDNA (787 bp) EcoRI-AvrII fragment is derived from plasmid (pXM) that contains also hIL-1α precursor cDNA but lacks the first 40 bp of the gene. This was the EcoRI-AvrII fragment. Those fragments were ligated into pMLP.TK that was digested with HindIII and XbaI. The resulting plasmid was named pMLP.hIL-1α (FIG. 12).

2.3 Characterization of pAd.hIl-1α

2.3.1 Sequence Analysis

The Il-1α precursor cDNA sequence of plasmid pMLP.hIl-1α has been determined completely, whereas the sequences flanking Il-1α precursor cDNA (SV40 poly(A) signal, major late promoter) have been sequenced partially to confirm whether the cloning procedures had not affected those area. As mentioned in the introduction, a polymorphism exists in human Il-1α protein. Sequence analysis indicated that the precursor cDNA we obtained encodes a protein which has Ser at position 114.

2.3.2 Transient Production of Human Il-1α in 293 Cells

Figure 13:
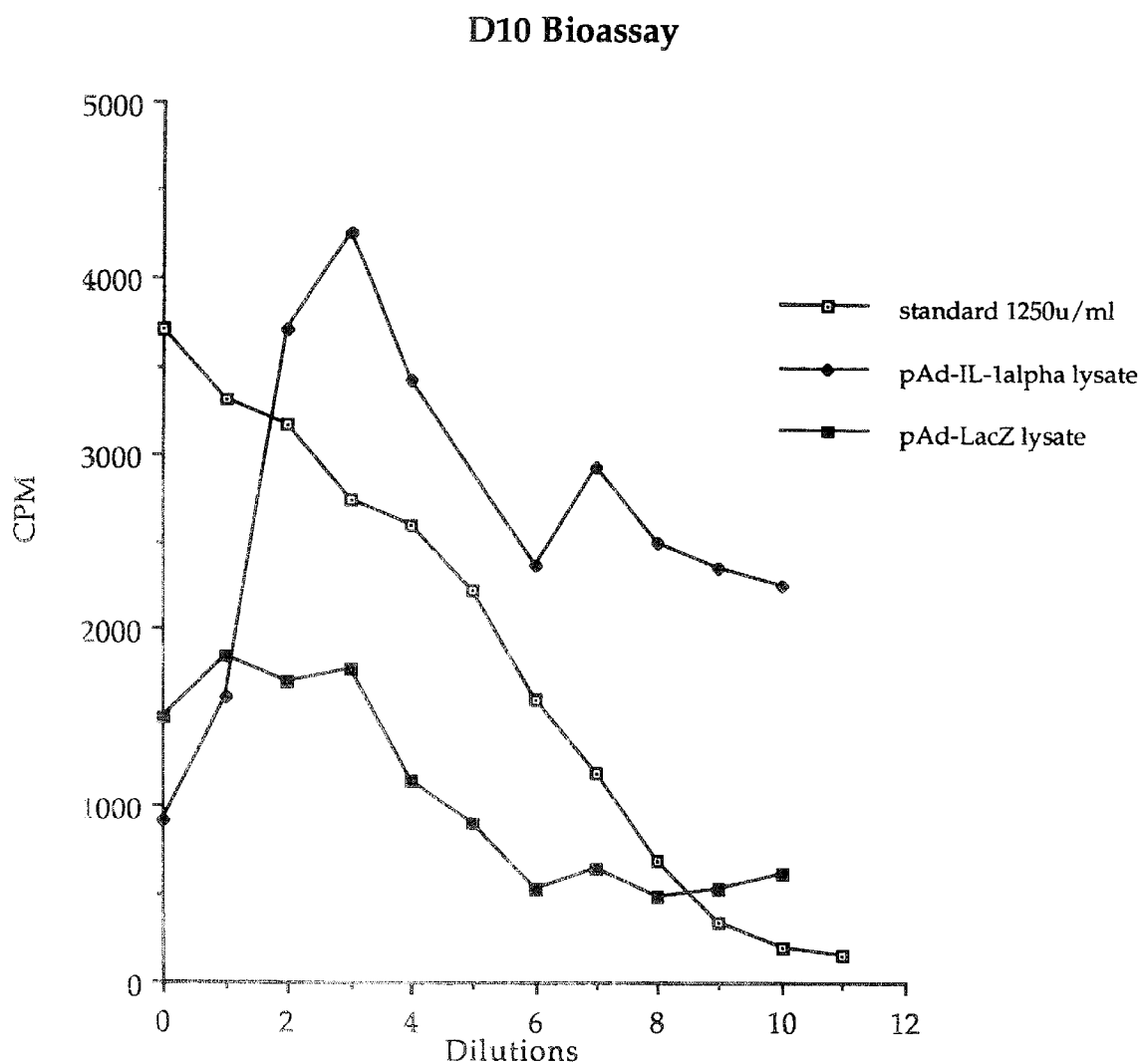
FIG. 13 shows transient production of human IL-1α in 293 (human embryo kidney) cells as tested in a bioassay using D10 cells. □ show standard 1250 u/ml; → show pAd-IL-1alpha lysate; and ■ show pAd-LacZ lysate.

To test whether plasmid pMLP.Il-1α was able to produce bioactive hIl-1α protein, it was transfected into 293 cells (human embryo kidney cells). 2 days after transfection the cells were harvested and the cell lysate was tested in a bioassay using D10 cells (60). The results of this experiment are presented in FIG. 13, and indicate that bio-active hIl-1a is produced after transfection of pMLP.Il-1α. Together with the sequencing data, this indicates that the pMLP.hIl-1α encodes functional hIl-1α.

Figure 8:
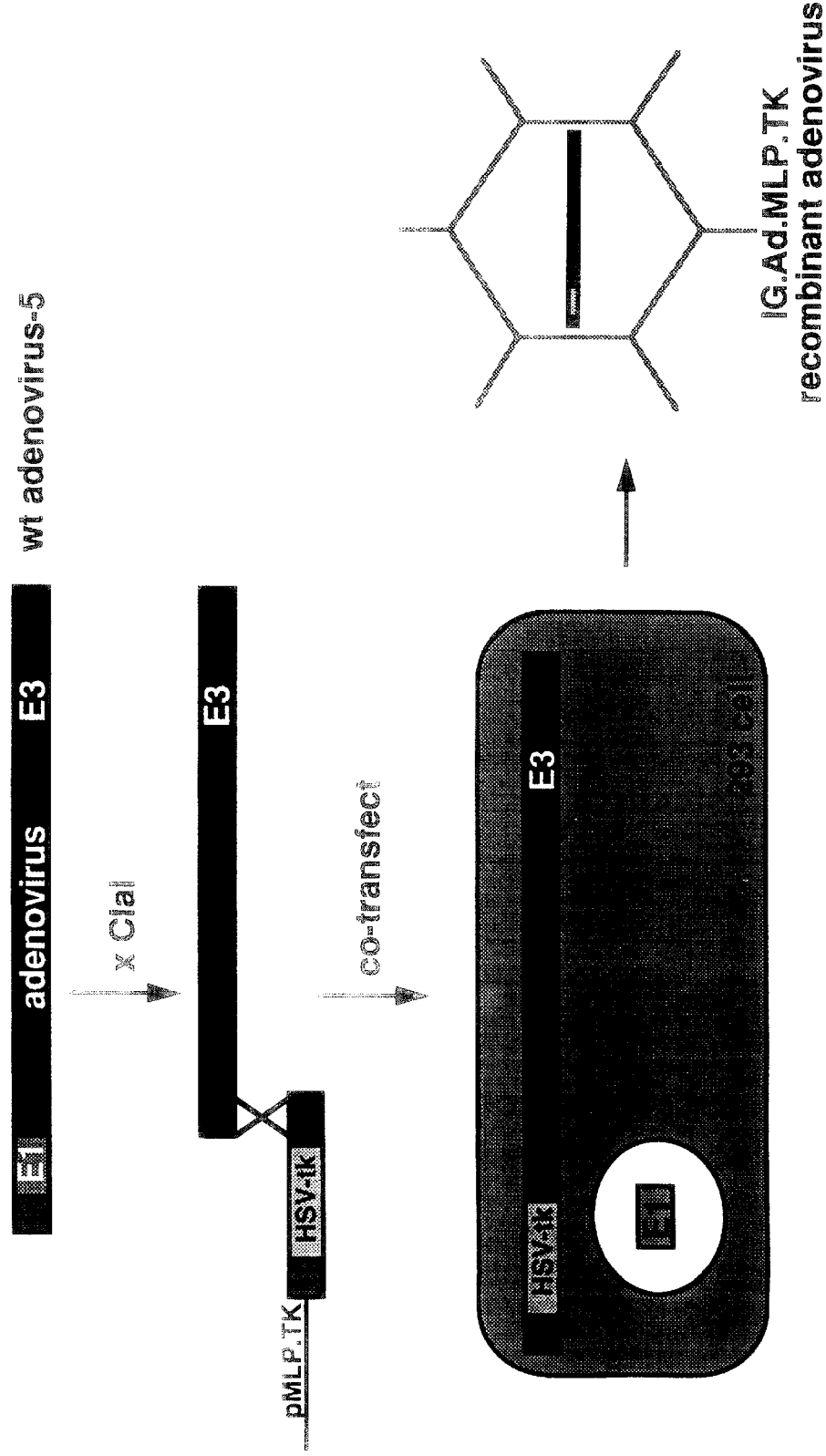
FIG. 8 shows construction of recombinant adenovirus IG.Ad.MLP.TK.

2.4 Construction and Production of Recombinant Adenovirus Harboring hIl-1α Precursor cDNA Recombinant adenovirus harboring human Il-1α precursor cDNA (IG.Ad.MLP.hIl-1α) was prepared by co-transfection of pMLP.hIl-1α and the large ClaI fragment of human adenovirus type 5, according to the scheme presented in FIG. 8 and as described before (see example 1). The functionality of the viruses was confirmed by measurement of hIl-1α in supernatant of 293 cells, using a commercially available ELISA kit (Quantikine, R & D systems).

2.5 Cloning of Rat Interleukin-3 (rIl-3) cDNA rIl-3 cDNA was isolated by transfecting COS cells with a construct harboring the rat Il-3 gene (pIlR1) (61). Two days later, total RNA was isolated from the cells and subjected to reverse transcription, using the following primer: rat Il-3 #2: 5'-ATGAGGATCCTTCAGGCTCCA-3' (SEQ ID NO:9) This primer introduces a BamHI site in the rIl-3 cDNA downstream of the translation stopcodon.

The resulting cDNA was PCR amplified using primer rat Il-3 #2 (described above) and rat Il-3 #1, the sequence of which is as follows:

rat Il-3 #1: 5'-ACAAAGCTTTGGAGGACCAG-3' (SEQ ID NO:10) This oligonucleotide introduces a HindIII site 5' to the ATG translation start codon.

The resulting PCR product was digested with BamHI and HindIII. HSV.TK from pMLP.TK was replaced by rIl-3 cDNA by digestion of pMLP.TK with HindIII and BamHI and ligating the HindIII/BamHI digested rat Il-3 cDNA. The rIl-3 cDNA in the resulting clone pMLP.rIl-3 was sequenced completely.

The rat Il-3 cDNA sequence (SEQ ID NO:10) is as follows:

AAGCTTTGGAGGACCAGAACGAGACAATGGTTCTTGCCAG

CTCTACCACCAGCATCCTCTGTATGCTGCTCCCGCTCCTG

ATGCTCTTCCACCAGGGACTCCAGATTTCAGACAGGGGCT

CAGATGCCCACCATTTACTCAGGACGTTGGATTGCAGGAC

TATTGCCTTGGAGATTTTGGTGAAGCTCCCATATCCTCAG

GTATCTGGACTCAATAATAGTGACGACAAAGCCAATCTGA

GGAATAGTACCTTGCGGAGAGTAAACCTGGACGAATTCCT

AAAAAGCCAAGAGGAGTTTGATTCTCAGGACACAACGGAC

ATCAAGTCCAAACTTCAGAAACTTAAGTGTTGTATTCCTG

CAGCTGCGAGCGACTCTGTGTTGCCAGGTGTCTACAATAA

AGATCTGGATGACTTTAAGAAGAAACTGAGATTCTACGTG

ATCCATCTTAAGGACCTGCAGCCAGTGTCAGTCTCTAGAC

CACCTCAGCCCACATCTAGCTCTGACAACTTTCGCCCTAT

GACCGTGGAATGTTAAAACAGCAGGCAGAGCAACTGGAGC

CTGAAGGATCC

The underlined sequences represent the introduced HindIII and BamHI sites that were use for cloning of the cDNA into pMLP.TK.

The sequence is homologous to the exons deduced from the genomic sequence (61), except that 3 additional aminoacids are encoded by our cDNA sequence that they were not indicated by (61). These sequences are found at the end of intron 1 in the genomic sequence (61), whereas we find them to be transcribed and thus belonging to the cDNA sequence. These sequences are dotted underlined in the sequence presented above.

Recombinant adenovirus harboring rIl-3 cDNA (IG.Ad.MLP.rIl-3) was generated according to the scheme presented in FIG. 8 and as described before for IG.Ad.MLP.TK.

IG.Ad.MLP.rIl-3 was assayed for production of functional rat Il-3 by subjecting 293 lysates for Il-3 activity. It was tested on FDCP-1 cells, which are dependent on (mouse) Il-3 or GM-CSF for growth (62). It turned out to be also sensitive for rat Il-3.

2.6 In Vivo Administration of Adenovirus Producing Cells to Experimental Rat Tumors In order to achieve maximal production of cytokines, adenovirus producing cells were injected directly into the tumor. The cytokines are expected to be produced then by the adeovirus producing cells and by tumor cells that are transduced by adenovirus released from the producers. The tumor model used was the L42 rat NSCLC in the Wag/Rij rat strain (63–65).

On day 1, L42 tumors were implanted subcutaneously in both flanks of the animals. Day 10, injection of $10^7$ 293 cells in a volume of 300 μl PBS, into the left flank tumors. The 293 cells were infected with recombinant adenovirus (m.o.i. 10) 48 hours before with recombinant adenoviruses listed below.

The rats were divided into five groups, each group containing 4 animals:

1—animals with only L42 tumors.
2—animals injected with non infected 293 cells
3—animals injected with 293 infected with IG.Ad.MLP.LacZ
4—animals injected with 293 infected with IG.Ad.MLP.rIL-3
5—animals injected with 293 infected with IG.Ad.MLP.hIL-1α

Before injection, the tumor sizes were measured. Average tumor volume: 130 mm³

The sizes of the tumors in both flanks were measured twice a week.

On day 20, the left flank tumors were injected again with 293 cells, exactly according to the scheme presented above. The tumor sizes were depicted as a function of time, and are presented graphically in FIGS. 14a–14j. The results show that regression of the contralateral tumor is seen only when cytokine (hIl-1α or rIl-3) harboring adenovirus is administered (¾ animals for each cytokine), suggesting that a host response against the tumor is elicited when high doses of cytokines are produced in the tumor.

2.7 Planned Use of Recombinant Adenoviruses Harboring hIl-1α or Il-3

Recombinant adenovirus harboring human Il-1α precursor cDNA or Il-3 cDNA sequences will be propagated to sufficient amounts and will be used for direct injection into solid tumors. Tumors that will be used in first instance will be NSCLC (non small cell lung cancer), but also mesothelioma, melanoma, glioma and other types of solid tumors will be investigated for carcinolysis and tumorimmunity after administration of recombinant adenoviruses harboring hIl-1α and/or Il-3 cDNA. A dose of virus (optimal dose to be determined in Phase I studies) will be injected either directly into the tumormass or it will be administered into metastasis of those tumors that are more amenable to apply the viruses. If the effect of injecting IG.Ad.MLP.hIl-1α itself is less than expected because release of hIl-1α protein is insufficient, virus instillation will be followed by local irradiation of the tumor, to achieve release of the produced reombinant hIl-1α. We also envisage to use IG.Ad.MLP.hIl-1α in combination with recombinant adenoviruses that harbor other cytokine genes or tumor suppressor genes. Alternatively, the treatment with hIl-1α will be combined with application of other recombinant adenoviruses such as IG.Ad.MLP.TK (recombinant adenovirus harboring Herpes Simplex Virus Thymidine kinase gene). Cells that express thymidine kinase can phosphorylate ganciclovir (which is not toxic to cells) into ganciclovir phosphate, which is toxic to cells. Cells that coexpress hIl-1α will release the intracellularly stored recombinant hIl-1α when dying, which will augment the anti-tumor effect. In addition to in vivo intra-tumoral injection of IG.Ad.hIl-1α or IG.Ad.Il-3, we also envisage to use the viruses also for vaccination type studies, either or not in combination with in vivo gene transfer of IG.Ad.hIl-1α or IG.Ad.Il-3. Tumor cells of a patient will be isolated, infected with IG.Ad.hIl-1α or IG.Ad.Il-3 irradiated and re-infused in the patient. Such an approach will be helpful in increasing the immunity against tumor cells. In addition, as shown in the example, we envisage to administer adenovirus-producing cells (e.g. 293) directly into tumors, which leads to a very high local production of hIl-1α or Il-3, both by the producer cells and the tumor cells that are transduced by viruses released by the virus producers.

References

1. Bout, A., Perricaudet, M., Baskin, G., Imler, J. L., Scholte, B. J., Pavirani, A., and Valerio, D. (1994) *Human Gene Therapy* 5, 3–10
2. Bout, A., Imler, J. L., Schulz, H., Perricaudet, M., Zurcher, C., Herbrink, P., Valerio, D., and Pavirani, A. (1994) *Gene Therapy* 1, 385–394
3. Haddada, H., Ragot, T., Cordier, L., Duffour, M. T., and Perricaudet, M. (1993) *Hum Gene Ther* 4(6), 703–11
4. Wold, W. S. M., and Gooding, L. R. (1991) *Virology* 184, 1–8
5. Ginsberg, H. S., Lundholm-Beauchamp, U., and Horswood, R. L. (1989) *Proc. natl. Acad. Sci. USA* 86, 3823–3827
6. Wold, W. S. M., Tollefson, A. E., and Hermiston, T. W. (1995) in Viroceptors, virokines and related immune modulators encoded by DNA viruses (McFadden, C., ed), pp. 147–185, Springer-Verlag, Heidelberg
7. Prince, G. A., Porter, D. D., Jenson, A. B., Horswood, R. L., Chanock, R. M., and Ginsberg, H. S. (1993) *J Virol* 67(1), 101–111
8. Ginsberg, H. S., Moldawer, L. L., Seghal, P. B., redington, M., and Killian, P. L. (1991) Proc. *Natl. Acad. Sci. USA* 88, 1651–1655
9. Stratford-Perricaudet, L. D., and Perricaudet, M. (1991) in Human Gene Transfer (Cohen-Adenauer, O., and Boiron, M., eds) Vol. 219, pp. 51–61, John Libbey Eurotext
10. Spergel, J. M., and Chen-Kiang, S. (1991) *J. Virol.* 6472–6476
11. Spergel, J. M., Hsu, W., Akira, S., Thimmappaya, B., Kishimoto, T., and Chen-Kiang, S. (1992) *J. Virol.* 66(2), 1021–1030
12. Engelhardt, J. F., Simon, R. H., Yang, Y., Zepeda, M., Weber-Pendleton, S., Doranz, B., Grossman, M., and Wilson, J. M. (1993) *Human Gene Therapy* 4, 759–769
13. Simon, R. H., Engelhardt, J. F., Yang, Y., Zepeda, M., Weber-Pendleton, S., Grossman, M., and Wilson, J. M. (1993) *Human Gene Therapy* 4, 771–780
14. Yang, Y., Nunes, F. A., Berencsi, K., Gonczol, E., Engelhardt, J. F., and Wilson, J. M. (1994) *Nat Genet* 7(3), 362–9
15. Engelhardt, J. F., Litzky, L., and Wilson, J. M. (1994) *Hum. Gene Ther.* 5, 1217–1229
16. Yang, Y., Nunes, F. A., Berencsi, K., Furth, E. E., Gonczol, E., and Wilson, J. M. (1994) *Proc Natl Acad Sci U S A* 91(10), 4407–11
17. Culver, K. W., Ram, Z., Wallbridge, S., Ishii, H., Oldfield, E. H., and Blaese, R. M. (1992) Science 256 (5063), 1550–2
18. Colombo, M. P., and Forni, G. (1994) *Imm. Today* 15, 48–51
19. Cansbacher, B., Bannerji, R., Daniels, B., Zier, K., Cronin, K., and Gilboa, E. (1990) *Cancer Res.* 50, 7820–7824
20. Takia, H. (1970) *J. Thorac Cardiovasc. Surg.* 59, 642–644
21. Ruckdeschel, J. C., Codish, S. D., Stranahan, A., and McKneally, M. F. (1972) *New Engl. J. Med.* 287(20), 1013–1017
22. McKneally, M. F., Maver, C., Kausel, H. W., and Alley, R. D. (1976) *J. Thorac Cardiovasc. Surg.* 72, 333–338
23. McKneally, M. F., Maver, C. M., and Kausel, H. W. (1977) Lancet 1, 1003
24. Bakker, W., Nijhuis-Heddes, J. M. A., Wever, A. M. J., Riviera, A. B. d. l., Velde, E. A. v. d., and Dijkman, J. H. (1981) *Thorax* 36, 870–874
25. Lowe, J., Iles, P. B., Shore, D. F., Langman, M. J. S., and Baldwin, R. W. (1980) *Lancet* 1, 11–13
26. Jansen, H. M., The, T. H., and Orie, N. G. M. (1980) Thorax 35, 781–787
27. McKneally, M. F., Maver, C., Bennet, J., and Ruckdeschel, J. (1980) in *II World conference on lung cancer* Copenhagen. Excerpta Medica, ICS 525 (Hansen, H. H., and Rorth, M., eds), pp. 108, Amsterdam
28. Amery, W. K., Cosemans, J., Gooszen, H. C., Cardozo, E. L., Louwagie, A., Stam, J., Swierenga, J., Vanderschueren, R. G., and Veldhuizen, R. W. (1979) *Cancer Immunol. and Immunother.* 7, 191–198
29. Hollinshead, A., Stewart, T. H. M., Takita, H., Dalbow, M., and Concannon, J. (1987) *Cancer* 60, 1249–1262
30. Dinarello, C. A., and Mier, J. W. (1987) *New Engl. J. Med.* 317, 940–945
31. Zöller, M., Douvdevani, A., Segal, S., and Apte, R. N. (1992) Int. *J. Cancer* 50, 443–449
32. Oppenheim, J. J., Kovacs, E. J., Matsushima, K., and Durum, S. K. (1986) *Immunol. Today* 7, 45–56
33. Schmidt, J. A., Mizel, S. B., Cohen, D., and Green, I. (1982) *J. Immunol.* 128, 2177
34. Mizel, S. B., Dayer, J. M., Krane, S. M., and Hergenhagen, S. E. (1981) *Proc. Natl. Acad. Sci. USA* 78, 2474
35. Baracos, V., Rodeman, H. P., Dinarello, C. A., and Goldberg, A. L. (1983) *N. Engl. J. Med.* 308, 553
36. March, C. J., Mosley, B., Larsen, A., Cerretti, D. P., Braedt, G., Price, V., Gillis, S., Henney, C. S., Kronheim, S. R., Grabstein, K., Conlon, P. J., Hopp, T. P., and Cosman, D. (1985) *Nature* 315, 641–646
37. Giri, J. G., Lomedico, P. T., and Mizel, S. B. (1985) *J. Immunol.* 134, 343–349
38. Singer, I. I., Scott, S., Hall, G. L., Limjuco, G., Chin, J., and Schmidt, J. A. (1988) *J. Exp. Med.* 167, 389–407
39. Bayne, E. K., Rupp, E. A., Lumjuco, G., Chin, J., and Schmidt, J. A. (1986) *J. Exp. Med.* 163, 1267–1280
40. Hazuda, D. J., Lee, J. C., and Young, P. R. (1988) *J. Biol. Chem* 263, 8473–8479
41. Kobayashi, Y., Yamamoto, K., Saido, T., Kawasaki, H., Oppenhein, J. J., and Matsushima, K. (1990) *Proc. Natl. Acad. Sci. USA* 87, 5548–5552
42. Carruth, L. M., Demczuk, S., and Mizel, S. B. (1991) *J. Biol. Chem.* 266(19), 12162–12167
43. Black, R. A., Kronheim, S. R., Merriam, J. E., March, C. J., and Hopp, T. P. (1989) *J. Biol. Chem.* 264, 5323–5326
44. Cerretti, D. P., Kozlosky, C. J., MOsley, B., Nelson, N., Ness, K. V., Greenstreet, T. A., March, C. J., Kronehim, S. R., Druck, T., Cannizzaro, L. A., Huebner, K., and Black, R. A. (1992) *Science* 256(5053), 97–100
45. Kurt-Jones, E. A., Fiers, W., and Pober, J. S. (1987) *J. Immunol.* 139, 2317–2324
46. Furutani, Y., Notake, M., Yamayoshi, M., Yamagishi, J., Nomura, H., Ohue, M., Furuta, R., Fukui, T., Yamada, M., and S, N. (1985) *Nucl. Acids Res.* 13(6), 5869–5882
47. Furutani, Y., Notake, M., Fukui, T., Ohue, M., Nomura, H., Yamada, M., and S, N. (1986) *Nucl. Acids Res.* 14(8), 3167–3179
48. Dechiara, T. M., Yound, D., Semionow, R., Stern, A. S., Batullo-Bernardo, C., Fiedler-Nagy, C., Kaffka, K. L., Killian, P. L., Yamazaki, S., Mitzel, S. B., and Lomedico, P. T. (1986) *Proc. Natl. Acad. Sci. USA* , 8303–8307
49. Matsushima, K., Taguchi, M., Kovacs, E. J., Young, H., and Oppenheim, J. J. (1986) *J. Immunol.* 136, 2883–2891
50. Mosley, B., Urdal, D. L., Prickett, K. S., Larsen, A., Cosman, D., Conlon, P. J., Gillis, S., and Dower, S. K. (1987) *J. Biol. Chem.* 262, 2941–2944
51. Jobling, S. A., Auron, P. E., Gurka, G., Webb, A. C., McDonald, B., Rosenwasser, L. J., and Gehrke, L. (1988) *J. Biol. Chem.* 263, 16372–16378

52. McKnight, S. L. (1980) Nucl. Acids Res. 8, 5949–5964
53. Levrero, M., Barban, V., Manteca, S., Ballay, A., Balsamo, C., Avantaggiati, M. L., Natoli, G., Skellekens, H., Tiollais, P., and Perricaudet, M. (1991) *Gene* 101(2), 195–202
54. Kalderon, D., Roberts, B. L., Richardson, W. D., and Smith, A. E. (1984) Cell 39, 499–509
55. Wet, J. R. D., Wood, K. V., DeLuca, M., Helinski, D. R., and Subramani, S. (1987) *Mol. Cell Biol.* 7, 725–737
56. Precious, B., and Russell, W. C. (1985) in *Virology: a practical approach* (Mahy, B., ed), pp. 193–205, Raven Press Ltd., Washington D.C.
57. Weizsaecker, M., Deen, D. F., Rosenblum, M. L., Hoshino, T., Gutin, P. H., and Barker, M. (1981) *J. Neurol.* 224, 183–192
58. Posner, J. B., and Chernik, N. L. (1978) Adv. *Neurol.* 19, 579–591
59. Byrnes, A. P., Rusby, J. E., Wood, M. J. A., and Charlton, H. M. (1995) *Neurosc.* 66(4), 1015–1024
60. Orencole, S. F., and Dinarello, C. A. (1989) Cytokine 1(1), 14–22
61. Cohen, D. R., Hapel, A. J., and Young, I. G. (1986) *Nucl. Acids Res.* 14, 3641–3658
62. Coligan, J. E., Kruisbeck, A. M., Margulies, D. H., Shevach, E. M., and Strober, W. (1991) in *Current Protocols in Immunology*, Greene and Wiley—Interscience, New York
63. Kal, H. B., Meijnders, P. J. N., Berkel, A. H. v., and Bekkum, D. W. V. (1991) In vivo 5, 301–306
64. Kal, H. B., Zurcher, C., and Bekkum, D. W. v. (1986) *J. Natl. Canc. Inst.* 76, 943–946
65. Kal, H. B., Berkel, A. H. v., Jong, B. v. d. V.-d., Bekkum, D. W. v., and Zurcher, C. (1988) *NCI monographs* 6, 111–114

What is claimed is:

1. A vector comprising;
a DNA sequence encoding an adenovirus genome which comprises a deletion of at least the E1 coding region and at least a deletion in the E3 coding region, but where said DNA sequence retains that portion of the E3 coding region which encodes the 14.7 kD protein such that expression of the 14.7 kD protein reduces a TNF response to a host cell infected with said adenoviral DNA sequence, and
a DNA sequence encoding a protein operably linked to a promoter.

2. The vector of claim 1, wherein the protein is selected from the group consisting of human interleukin-1α, interleukin-3 and thymidine kinase.

3. The vector of claim 1 wherein said DNA sequence encodes for the protein human interleukin-1α.

4. The vector of claim 1 wherein said DNA sequence encodes for the protein thymidine kinase.

5. The vector of claim 1 wherein said DNA sequence encodes for the protein interleukin-3.

6. A vector comprising:
a DNA sequence encoding an adenovirus genome from which the E1a coding region has been deleted, wherein said DNA sequence comprises a deletion in the E3 coding region, but retains that portion of the E3 coding region which encodes the 14.7 kD proteins such that expression of the 14.7 kD protein reduces a TNF response to a host cell infected with said adenoviral DNA sequence.

7. The vector of claim 6, further comprising a DNA sequence encoding a gene product other than an adenovirus gene product.

8. The vector of claim 7, where in the gene product is a protein.

9. The vector of claim 8, wherein the protein selected from the group consisting of cytokines, suicide gene proteins.

10. The vector of claim 7, wherein the gene product is mRNA.

11. The vector of claim 6, wherein said adenovirus DNA is selected from DNA of an adenovirus type 5 or of an adenovirus type 2.

12. An isolated mammalian cell exhibiting a reduced TNF response, wherein the cell comprises a vector which itself comprises a DNA sequence encoding an adenovirus genome from which the E1a promoter has been deleted and a deletion in the E3 coding region, but retains a portion of the E3 coding region that encodes the 14.7 kD proteins such that expression of the 14.7 kD protein reduces a TNF response to a host cell infected with said adenoviral DNA.

13. A vector comprising:
a replication-defective adenovirus comprising a DNA sequence encoding an adenovirus genome which comprises a deletion of at least the E1a coding region, where said DNA sequence comprises at least one further deletion in a non-essential region, but wherein said DNA sequence retains a portion of the E3 coding region that encodes a functional 14.7 kD protein such that expression of the 14.7 kD protein reduces a TNF response to a host cell infected with said vector.

14. The vector of claim 13, further comprising a DNA sequence encoding a gene product other than an adenovirus gene product operably linked to a promoter.

15. The vector of claim 14, wherein the gene product is a protein.

16. The vector of claim 15, wherein said protein is from the group consisting of cytokines and suicide gene proteins.

17. The vector of claim 14, wherein the gene product is mRNA.

18. The vector of claim 13, wherein said DNA sequence comprises an adenovirus E4 region.

19. An isolated mammalian cell compromising the vector of claim 13.

20. A DNA construct comprising a DNA sequence encoding an adenovirus genome which comprises:
a deletion of at least an E1 coding region;
a deletion in the E3 coding region, but retaining the E3 sequence encoding the 14.7 kD protein which when produced reduces the a mammalian TNF response to a cell infected with the construct; and
a DNA sequence encoding a heterologous, non-adenovirus gene product operably linked to a promoter.

21. The construct of claim 20, wherein the gene product is protein.

22. The construct of claim 21, wherein the protein is selected from the group consisting of cytokines and suicide gene proteins.

23. The construct of claim 20, wherein the gene product is mRNA.

24. An isolated mammalian cell comprising the DNA construct of claim 20.

25. A vector comprising:
DNA sequences from one or more adenovirus genomes, from which at least the E1 region, including the E1a promoter, is lacking, and which comprises a fragment of the E3 coding region that encodes the 14.7 kD protein such that when the 14.7 kD protein is expressed the TNF response to a mammalian cell comprising said vector is reduced.

26. The vector of claim 25, further comprising:
a DNA sequence encoding a gene product other than an adenovirus gene product operably linked to expression regulatory elements.

27. The vector of claim 26, wherein the expression regulatory elements is a CMV promoter.

28. The vector of claim 26, wherein said DNA sequence encodes a protein.

29. The vector of claim 26, wherein said DNA sequence is a gene is selected from the group consisting of suicide genes and cytokine genes.

30. The vector of claim 29, wherein said suicide gene is the thymidine kinase gene of a herpes simplex virus.

31. The vector of claim 29, wherein said cytokine gene is a human interleukin-1α gene.

32. The vector of claim 29, wherein said cytokine gene is a human interleukin-3 gene.

33. An adenoviral vector comprising:
a DNA sequence encoding an adenovirus genome from which at least all of the E3 coding region except for that portion of E3 which encodes the 14.7 kD protein, has been deleted and from which at least the E1a promoter has been deleted, wherein expression of the 14.7 kD protein results in decrease in the TNF response to host cell comprising said vector.

34. An adenoviral vector comprising:
a DNA sequence encoding an adenovirus genome from which at least all of the E3 coding region except for that portion of E3 which encodes the 14.7 kD protein, has been deleted and from which at least the E1 region has been deleted, wherein expression of the 14.7 kD protein results in decrease in the TNF response to host cell comprising said vector.

* * * * *

UNITED STATES PATENT AND TRADEMARK OFFICE
CERTIFICATE OF CORRECTION

PATENT NO. : 6,204,052 B1
DATED : March 20, 2001
INVENTOR(S) : Abraham Bout, Dirk W. Van Bekkum and Domenico Valerio It is certified that error appears in the above-identified patent and that said Letters Patent is hereby corrected as shown below:

<u>Title page,</u>
Item [75], Inventors, after "Bout," change "Moenkepelle" to -- Moerkapelle -- change "Van" to -- van --

<u>Column 2,</u>
Line 28, after "proteins" change "is" to -- are --

<u>Column 3,</u>
Line 53, after "levels" insert -- of --

<u>Column 4,</u>
Line 20, after "capable" change "or" to -- of --
Line 61, insert a comma after "(gene)"

<u>Column 7,</u>
Line 52, insert a period after "treatments"
Line 54, insert a period after "tumor"

<u>Column 8,</u>
Line 5, change "MLPtpl" to -- MLP\tpl --

<u>Column 11,</u>
Line 14, change "andligated" to -- and ligated --

<u>Column 12,</u>
Line 60, change "13-days" to -- 13-day --
Line 66, change "sacrified" to -- sacrificed --
Line 66, change "spresence" to -- presence --

UNITED STATES PATENT AND TRADEMARK OFFICE
CERTIFICATE OF CORRECTION

PATENT NO. : 6,204,052 B1
DATED : March 20, 2001
INVENTOR(S) : Abraham Bout, Dirk W. Van Bekkum and Domenico Valerio It is certified that error appears in the above-identified patent and that said Letters Patent is hereby corrected as shown below:

Column 13,
Line 1, change "diafragma" to -- diaphragm --

Column 14,
Line 7, change "$^9$L" to -- 9L --

Column 15,
Line 11, after "of" and before "group" insert -- the --

Column 16,
Line 32, change "area" to -- areas --
Line 63, change "stopcodon" to -- stop codon --

Column 17,
Line 39, after "that" delete "they"

Column 18,
Lines 5, 7 and 9, after "293" insert -- cells --
Line 36, change "tumormass" to -- tumor mass --

Column 19,
Line 17, change "C." to -- G. --

UNITED STATES PATENT AND TRADEMARK OFFICE
CERTIFICATE OF CORRECTION

PATENT NO.    : 6,204,052 B1
DATED         : March 20, 2001
INVENTOR(S)   : Abraham Bout, Dirk W. Van Bekkum and Domenico Valerio It is certified that error appears in the above-identified patent and that said Letters Patent is hereby corrected as shown below:

Column 22,
Line 12, change "V." to --v.--

Column 27,
Line 54, after "proteins" and before "selected" insert -- is --

Signed and Sealed this

Twenty-second Day of July, 2003

JAMES E. ROGAN
*Director of the United States Patent and Trademark Office*